United States Patent
Siegel

(10) Patent No.: US 9,321,242 B1
(45) Date of Patent: *Apr. 26, 2016

(54) FLUID HANDLING DEVICE AND METHOD

(71) Applicant: David R. Siegel, Warren, NJ (US)

(72) Inventor: David R. Siegel, Warren, NJ (US)

( * ) Notice: Subject to any disclaimer, the term of this patent is extended or adjusted under 35 U.S.C. 154(b) by 111 days.

This patent is subject to a terminal disclaimer.

(21) Appl. No.: 14/065,660

(22) Filed: Oct. 29, 2013

Related U.S. Application Data

(63) Continuation-in-part of application No. 12/869,305, filed on Aug. 26, 2010, now Pat. No. 8,663,782.

(60) Provisional application No. 61/287,255, filed on Dec. 17, 2009.

(51) Int. Cl.
*B32B 3/30* (2006.01)

(52) U.S. Cl.
CPC .......................................... *B32B 3/30* (2013.01)

(58) Field of Classification Search
CPC .................................. Y10T 428/24479; Y10T 428/24496–428/24512; Y10T 428/2457; A61G 13/102; A47L 23/266; A61B 19/088
USPC ............................. 428/78, 156, 158–160, 167
See application file for complete search history.

(56) References Cited

U.S. PATENT DOCUMENTS

| | | | |
|---|---|---|---|
| 2,005,659 A | 6/1935 | Matteson | |
| 2,014,268 A | 9/1935 | Tenney | |
| 2,720,766 A | 10/1955 | Helburn | |
| 4,765,670 A | 8/1988 | Jackson | |
| 4,811,937 A | 3/1989 | Rothman | |
| 5,028,468 A | 7/1991 | Taylor | |
| 5,080,956 A | 1/1992 | Smith | |
| 5,151,314 A * | 9/1992 | Brown | 428/198 |
| 6,102,073 A | 8/2000 | Williams | |
| 6,245,697 B1 | 6/2001 | Conrad et al. | |
| 6,568,419 B1 | 5/2003 | Robinson et al. | |
| 6,599,615 B2 | 7/2003 | Burke et al. | |
| 6,719,348 B1 | 4/2004 | Song | |
| 6,726,190 B2 | 4/2004 | Malpass et al. | |
| 7,078,088 B2 | 7/2006 | Price et al. | |
| 7,291,376 B1 | 11/2007 | Siegel et al. | |

(Continued)

FOREIGN PATENT DOCUMENTS

JP 2005254838 A 9/2005

OTHER PUBLICATIONS

Partial Machine Translation of JP2005254838.
(Continued)

*Primary Examiner* — Alexander Thomas
(74) *Attorney, Agent, or Firm* — Thomas L. Adams

(57) ABSTRACT

Fluids are handled with a discardable floormat stacked with an absorbent sheet that extends beyond the floormat. The floormat is compressible and resilient, and may be a single or multiple sections. Atop the floormat are trip-avoiding channels feeding a gutter on a side whose height equals or exceeds the opposite side. The floormat has a border region, and a greater central region that is flat except for the channels. The border region has a height not exceeding that of the gutter, which has a draining outlet. In some cases the gutter is mostly free to fill fully and form a single exposed stream. In other cases, tubing occupies most of the gutter length, and has some intake apertures. Fluid entering the tubing can be sucked out, while fluid arriving at the absorbent sheet will be absorbed.

20 Claims, 14 Drawing Sheets

(56) References Cited

U.S. PATENT DOCUMENTS

| | | | |
|---|---|---|---|
| 8,839,812 B2* | 9/2014 | Tanhehco et al. | 137/312 |
| 2002/0092563 A1 | 7/2002 | Robinson | |
| 2003/0068463 A1 | 4/2003 | Polley | |
| 2003/0232175 A1 | 12/2003 | Zahler | |
| 2004/0091674 A1 | 5/2004 | Altshuler | |
| 2006/0029773 A1 | 2/2006 | Waterman et al. | |
| 2006/0070654 A1 | 4/2006 | VanBasten | |
| 2008/0178957 A1 | 7/2008 | Thomas et al. | |

OTHER PUBLICATIONS

My Name is Martha Marshall, artistsjournal.wordpress.com, dated Jul. 2, 2007.

We look Forward to Seeing You, flagshipsurgical.com, dated Sep. 26, 2011.

* cited by examiner

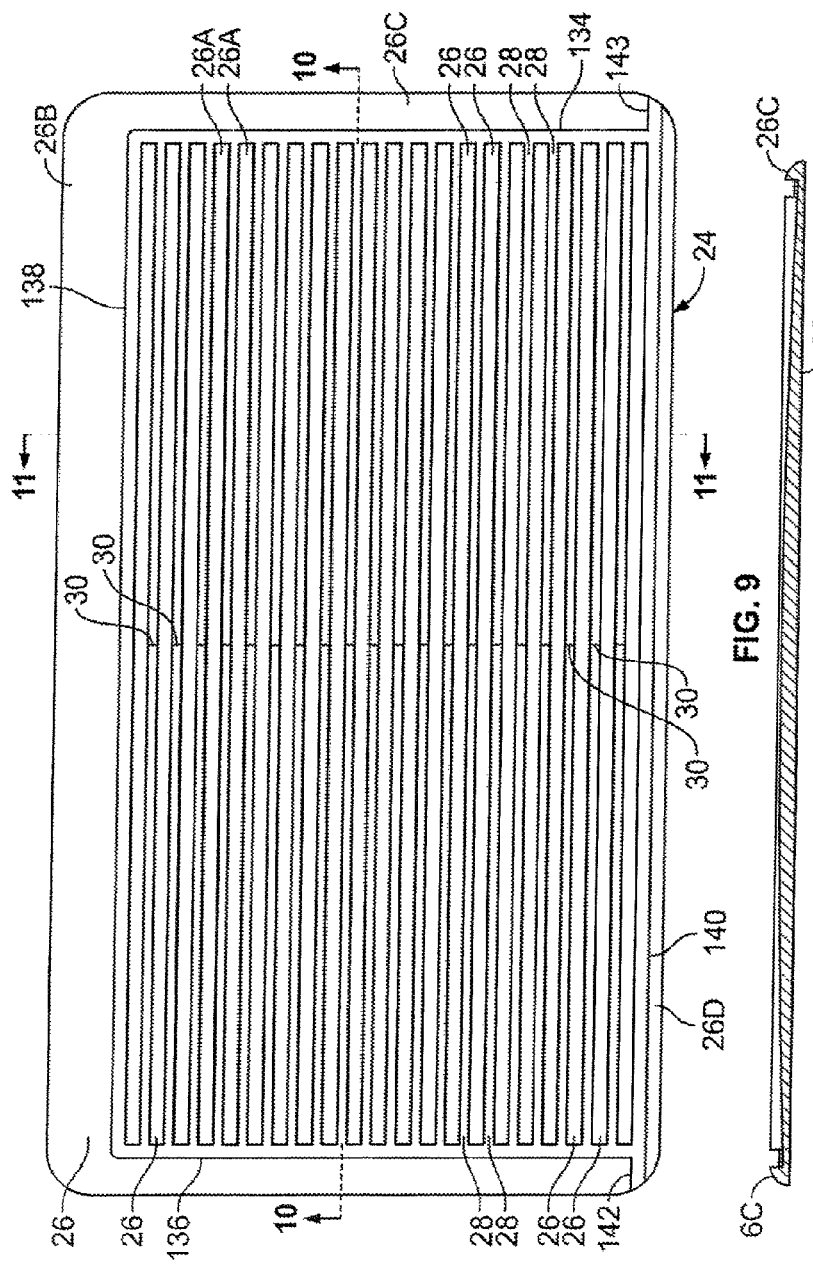
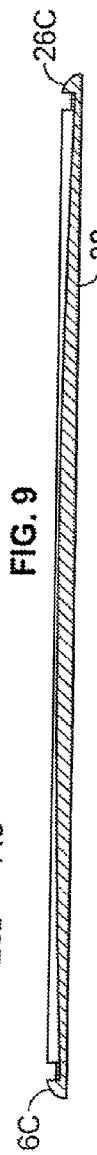
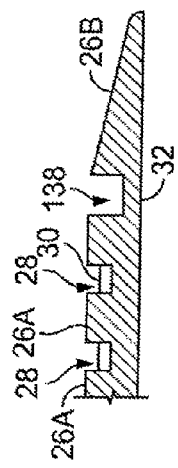
FIG. 9
FIG. 10
FIG. 11

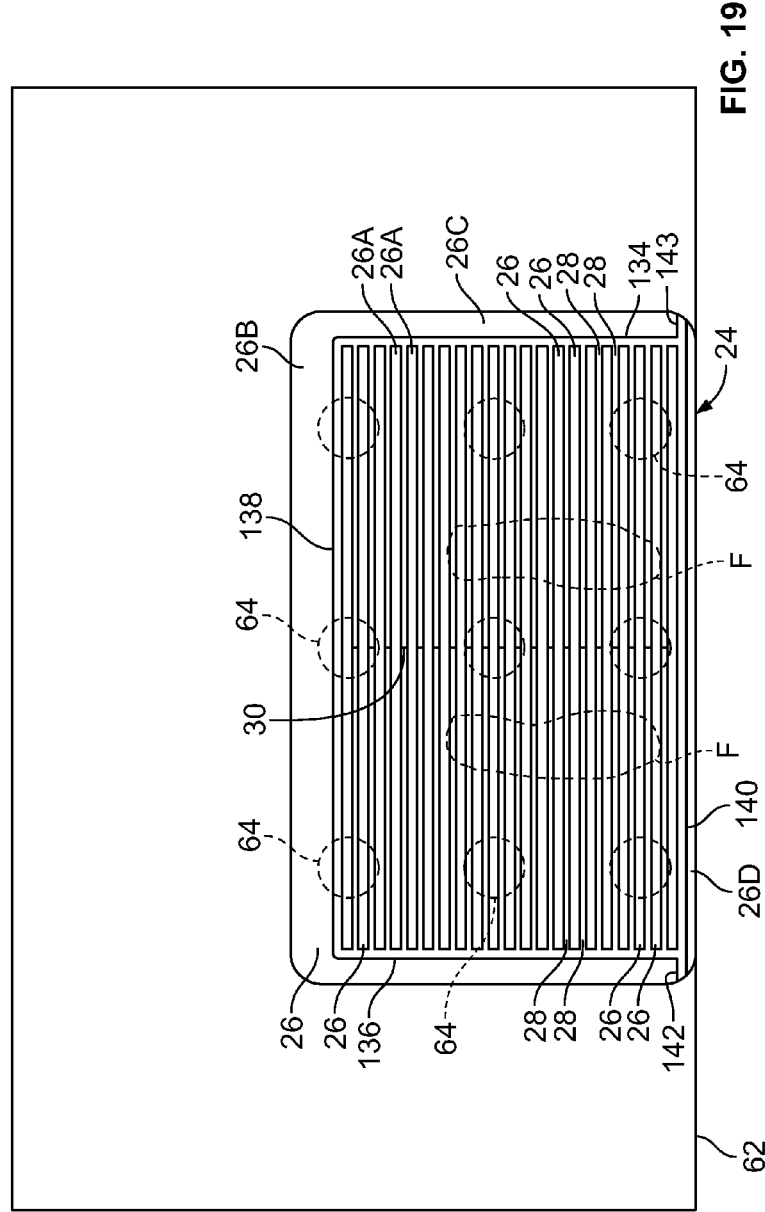
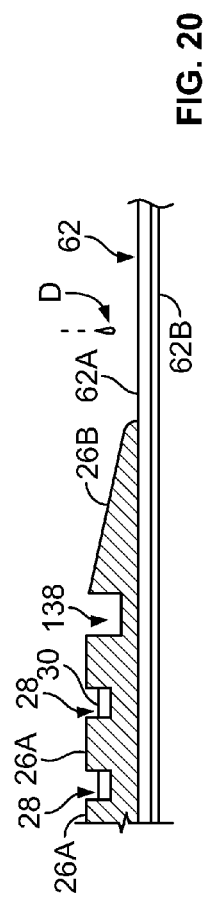

FLUID HANDLING DEVICE AND METHOD

CROSS REFERENCES TO RELATED APPLICATIONS

This application is a continuation-in-part application of U.S. patent application Ser. No. 12/869,305 filed 26 Aug., 2010 (now U.S. Pat. No. 8,663,782), which claims the benefit of U.S. Provisional Patent Application, Ser. No. 61/287,255, filed 17 Dec. 2009, the contents of which are hereby incorporated by reference herein.

BACKGROUND OF THE INVENTION

1. Field of the Invention

The present invention relates to materials and methods for handling fluids released during a procedure or in various other environments.

2. Description of Related Art

During various procedures fluids are released, which often fall onto the floor. For example, during a surgical procedure, not only can blood and other body fluids spill onto the floor, some procedures irrigate a surgical site with copious amounts of saline solution, which is then allowed to spill onto the floor.

It is highly desirable to quickly get these fluids away from the surgeon's feet to reduce the risk of slipping. Also, fluids released during surgery can spread infections and this risk is greatly enhanced the longer the surgeon stands or walks in these fluids. In the past surgical assistants have used existing surgical suction devices to vacuum these fluids. However, this method is not only inefficient but produces much distracting noise. Other known methods include placing towels or blankets on the fluid puddles, but this is time-consuming and requires the surgeon to step away and then stand on soaking material, which is both uncomfortable and increases the risk of tripping, as well as infection.

In addition, musculoskeletal disorders (MSDs) resulting from prolonged standing in the work place present not only a challenge to our health system in economic terms (workers compensation claims), but also place a significant burden upon the productivity, safety and health of the individual worker in the health-care environment. MSDs are injuries and illnesses that affect muscles, nerves, tendons, ligaments, cartilage and joints, spinal discs, blood vessels and bones. MSDs are not usually caused by acute trauma, but occur slowly over time due to repeated trauma to the soft tissues. Work-Related Musculoskeletal Disorders (WMSDs) are MSDs that are caused or made worse by work methods and environment. WMSDs can occur when the physical capabilities of the worker do not match the physical requirements of the job. The discomfort due to a WMSD often improves following medical treatment. Changing the work environment in order to alleviate stresses which led to the symptoms will help as well.

There have been many independent journal articles & studies, most focusing on the benefits of anti-fatigue matting (ergonomics) utilized in the work place. For example, OSHA (Occupational Safety and Health Administration) has identified static posture, contact stress and awkward postures as some of the potential workplace risk factors that cause MSDs. In the repealed AOSHA-Ergonomic Program Final rule, prolonged and static standing was identified as a risk factor and anti-fatigue matting was a control method for that risk factor.

Various other environments exist where a person may be standing during a procedure and where fluid may be spilled in the vicinity of where the person stands. For example, boaters may stand on a deck that is periodically sprayed or splashed by seawater. In some cases the boater may need to operate, repair or clean equipment and seawater may drain from the equipment during the procedure.

Also fishermen and hunters may need to clean, dress and prepare their catch or kill. In such cases fluids may run onto the ground or floor due to the release of body fluids or water used to clean the work site. Butchers will experience a similar situation when cutting and dressing meat at a butcher shop.

In addition, many technicians and hobbyists in the automotive field, gun repair/maintenance field, or other mechanical repair fields may spill fluids used to clean parts or may spill fluids used by the machinery (hydraulic fluid, coolant, brake fluid, transmission fluid, refrigerant, etc.)

Ordinary consumers may also deal with spills in the vicinity of where the person stands. Spilled fluids are often encountered when preparing foods or using the sink in a kitchen. In addition, various cleaning or repair tasks conducted throughout the house, yard or garden may involve fluid spills as well.

In U.S. Pat. No. 4,765,670 an auto mat has a number of grooves that all slope in the same direction to fill a sump formed along one edge of the mat. The reference recognizes that this sump can overflow and therefore suggests connecting the sump to a drainage tank.

In U.S. Pat. No. 6,719,348 flooring 10 is installed over a number of storage compartments 42 in the back of a motor vehicle. The top of the flooring has a number of grooves 16 arranged in a herringbone pattern and feeding two central channels 14. Fluids falling on the flooring 10 flow through grooves 16 and channels 14 into a sump 40 built into the rear of the vehicle.

In U.S. Patent Application 2002/0092563 a crowned, non-absorbent splash pad 42 is placed on a base with raised center 26 and radial drainage channels 28, which feed into lower peripheral channel 30. Fluid-removing suction tubing 50 is connected to the lower channel 30. The base is not meant to support the weight of a person.

In U.S. Patent Application 2003/0068463 a disposable, surgical floormat can be affixed to a surface using adhesive material 28 attached to a carrier sheet 26 and protected with removable liner sheet 29. Cover 60 provides a non-slip, water-resistant surface, while layers 30, 40, 50 gradually decrease in overall length and width, creating a Apyramid effect.

In FIG. 6 of U.S. Patent Application 2004/0091674 a corrugated anti-fatigue mat has drainage holes 240.

In U.S. Pat. No. 4,811,937, operating room personal stand on a floor through which fluids pass to a slightly inclined fluid receiving surface. Fluids are directed into a trough, and evacuated through a drain which is connected to a suction device.

In U.S. Pat. No. 6,102,073 a porous, flexible mat 34 rests atop a grid 32. The grid 32 is supported by a base 12 with studs 30, which defines a floor 20 formed of three sloped segments 22, 24, and 26 along which fluids will flow. Fluids directed onto the mat will flow onto the floor 20, where they will be withdrawn through fluid outlet 28 by a suitable suction device.

In U.S. Pat. No. 6,568,419, a broad, shallow vessel 28 is used to collect fluids that pass through a foot pad 24 made of a sturdy, non-woven mat 54 that operating room personnel stand on. Fluids are removed from the vessel 28 by a drainage system 26 and stored in a collection tank 80.

In U.S. Patent Application 2003/0232175 a floor mat 100 has four folding panels 110, 120, 130, 135 with fluid-capturing recesses 290 and beveled edges 295.

In U.S. Pat. No. 6,726,190, suction cups 26 on the bottom surface 14 of a mat 20 restrict movement on the floor, and fluids can pass into holes 30 in the mat.

In U.S. Pat. No. 5,080,956 a non-porous sheet 30 made of bubble-pack material channels liquids 34 onto absorbent sheet 20.

In U.S. Pat. No. 5,028,468 a thin plastic layer 16 is inserted into an envelope 12 with an absorbent surface 14 to provide an anti-fatigue surface for surgical personnel and a means of floor protection from fluids. The thin plastic layer 16 can be removed and re-used, while the envelope 12 is discarded after each use.

In U.S. Pat. No. 6,245,697, protective, flexible mats are used for absorbing liquids, and may contain non skid material.

See also references cited in related cases, cited above.

SUMMARY OF THE INVENTION

In accordance with the illustrative embodiments demonstrating features and advantages of the present invention, there is provided a device for handling fluids. The device has a floormat with an opposing pair of surfaces, including a topside and an underside. The floormat is formed, at least in part, of compressible and resilient material. The topside has a spaced plurality of channels feeding at least one gutter on a side of the gutter that has a height at least as great as the opposite side thereof. The channels are sized to avoid a risk of tripping. The topside has a central region and a border region. The central region occupies most of the topside and is substantially flat throughout except for the channels. The border region has a height no greater than that of the at least one gutter. The at least one gutter has at least one outlet for draining fluid from the gutter. The at least one gutter over most of its length is free from obstruction that would prevent fluid from fully filling the gutter and forming a single stream that is exposed on top. The device also has an absorbent sheet attached to a given one of the opposing surfaces of the floormat. At least part of the absorbent sheet is stacked to extend peripherally beyond the floormat.

According to yet another aspect of the invention a device is provided for handling fluids. The device has a floormat with an opposing pair of surfaces, including a topside and an underside. The floormat is formed, at least in part, of compressible and resilient material. The topside has a spaced plurality of channels feeding at least one gutter on a side of the gutter that has a height at least as great as the opposite side thereof. The channels are sized to avoid a risk of tripping. The topside has a central region and a border region. The central region occupies most of the topside and is substantially flat throughout except for the channels. The border region has a height no greater than that of the at least one gutter. The at least one gutter has at least one outlet for draining fluid from the gutter. The device has tubing lying in the at least one gutter and occupying at least most of its length. The tubing has one or more intake apertures located downstream of at least some of the plurality of channels. The device also has an absorbent sheet attached to a given one of the opposing surfaces of the floormat. At least part of the absorbent sheet is stacked to extend peripherally beyond the floormat.

According to yet another aspect of the invention a device is provided for handling fluids. The device has a floormat and an interconnected pair of tubes. The floormat includes an abutting pair of mat sections formed, at least in part, of compressible and resilient material. Each of the mat sections has on top, one or more intermediate gutters and upstream therefrom a spaced plurality of channels. The interconnected pair of tubes lies in the one or more intermediate gutters of a different corresponding one of the pair of mat sections.

According to still yet another aspect of the invention a method is provided for handling fluids released during a procedure. The method employs an absorbent sheet and a floormat with a drainage gutter containing perforated tubing. The method includes the step of placing the floormat and absorbent sheet where a user is expected to stand during the procedure. The floormat and absorbent sheet are stacked with at least part of the absorbent sheet extending beyond the floormat. The perforated tubing occupies most of the length of the drainage gutter. Another step is sucking out of the tubing, fluid entering the tubing through its perforations. The method also includes the step of standing atop the floormat and absorbent sheet during at least part of the procedure. Another step is absorbing into the absorbent sheet, fluids that arrive onto the absorbent sheet during the procedure. The method also includes the steps of vacating the floormat and absorbent sheet, and discarding the floormat and absorbent sheet before starting another procedure.

By employing equipment and methods of the foregoing type, fluids released during surgery or other procedures can be handled in a highly effective and efficient manner. In one embodiment a rectangular floormat with rounded corners is made of an elastomeric, material for reducing fatigue and increasing comfort. The mat overlays an absorbent sheet. In some simple embodiments the floormat may have a flat topside and underside.

In another embodiment the floormat has a relatively flat topside, except for a number of longitudinal channels. The floors of these channels are sloped away from a central peak so that fluids released during a procedure flow into the channels and away from the center of the mat. For this embodiment, the floormat has rounded corners and is formed of a compressible and resilient material to reduce a user's fatigue.

In another embodiment, the floormat has a crowned central section, which is integral with a tapered apron that encircles the central section. The apron is formed with a number of shallow channels that run from the outside border of the central section to the edge of the apron.

In the latter two embodiments fluids eventually drain into a gutter that runs along the periphery of the mat. The gutter can have one or more outlet gutters so that the fluid can drain to a single location away from the mat. In one embodiment, the gutter can be fitted with drainage pipes that lead to the outlet gutter. In a disclosed embodiment these drainage pipes will have apertures that are aligned with drainage channels and the pipes can be covered with a material that acts as a filter and noise suppressor. A suction hose can be attached to the drainage pipes to draw away the draining fluid.

All of these floormats can be stacked together with an absorbent sheet. The absorbent sheet is typically longer and wider than the floormat and will extend peripherally away from at least three sides of the floormat. In some embodiments the front edges of the floormat and absorbent sheet will be coterminous so the absorbent sheet does not impinge upon obstructions in the work area, such as the legs of a surgical table.

In the disclosed embodiment, the absorbent sheet has a fluid impermeable layer laminated to an absorbent layer. This fluid impermeable layer may have a slip resistant surface to avoid falls. The floormat and absorbent sheet can be attached by adhesive or mechanical fasteners or, in some cases, remain unattached so their relative positions can be easily adjusted.

Fluid that may spill during a procedure can be absorbed by the absorbent sheet, either directly or indirectly after draining off the floormat. In some embodiments fluids falling on the floormat can be removed by a suction tube connected to drainage pipes installed on the floormat.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein:

FIG. 9 is a plan view of a floormat that is an alternate to those described above; and FIG. 10 is a sectional view taken long line 10-10 of FIG. 9;

FIG. 11 is a cross-sectional view taken long line 11-11 of FIG. 9 of a fragment of the floormat;

FIG. 19 is a plan view of a device employing the floormat of FIG. 9 overlaying an absorbent sheet, in accordance with principles of the present invention;

FIG. 20 is a cross-sectional view of a fragment of the device of FIG. 19;

DETAILED DESCRIPTION OF THE PREFERRED EMBODIMENTS

Figure 1:
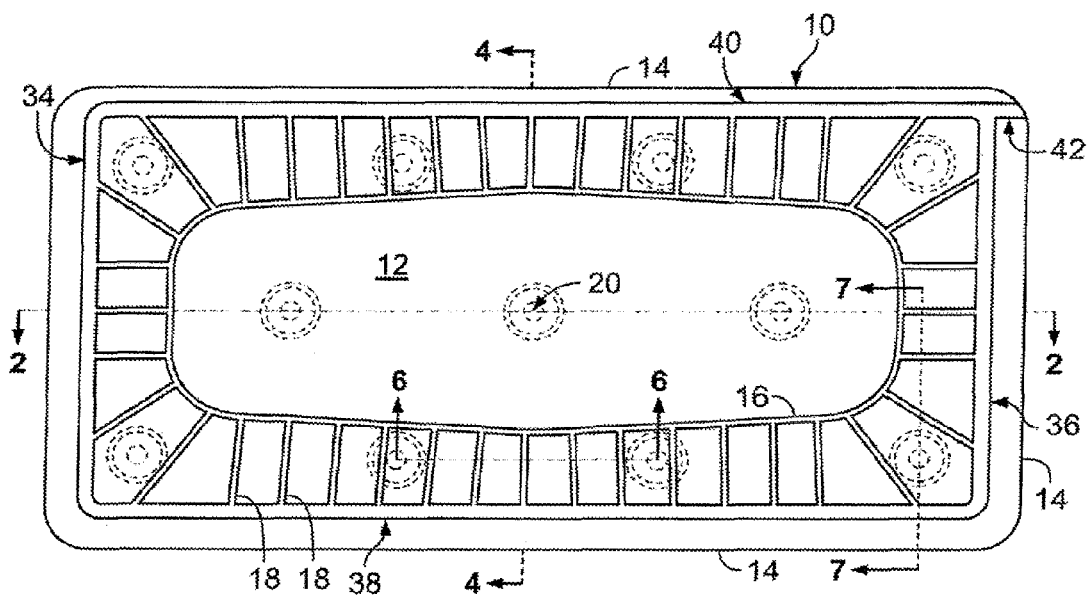
FIG. 1 is a plan view of a floormat in accordance with the present invention.
Figure 2:
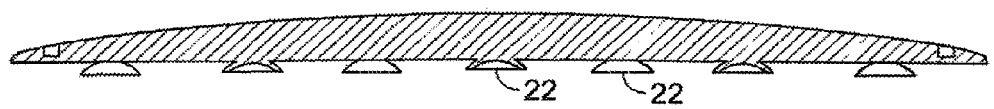
FIG. 2 is a cross-sectional view taken a long line 2-2 of FIG. 1.
Figure 3:
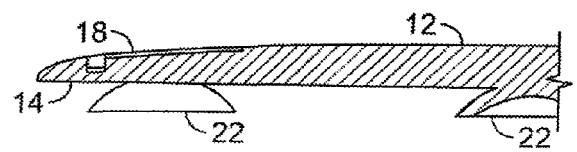
FIG. 3 is detailed, fragmentary, cross-sectional view of the left portion of the floormat of FIG. 2.
Figure 4:
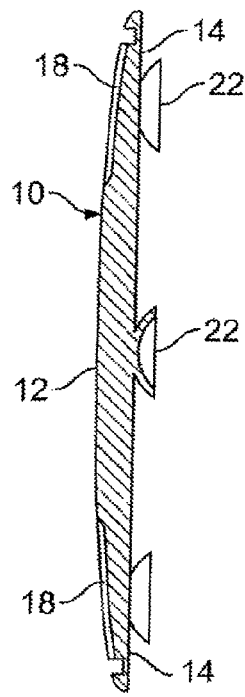
FIG. 4 is a cross-sectional view taken a long line 4-4 FIG. 1.
Figure 5:
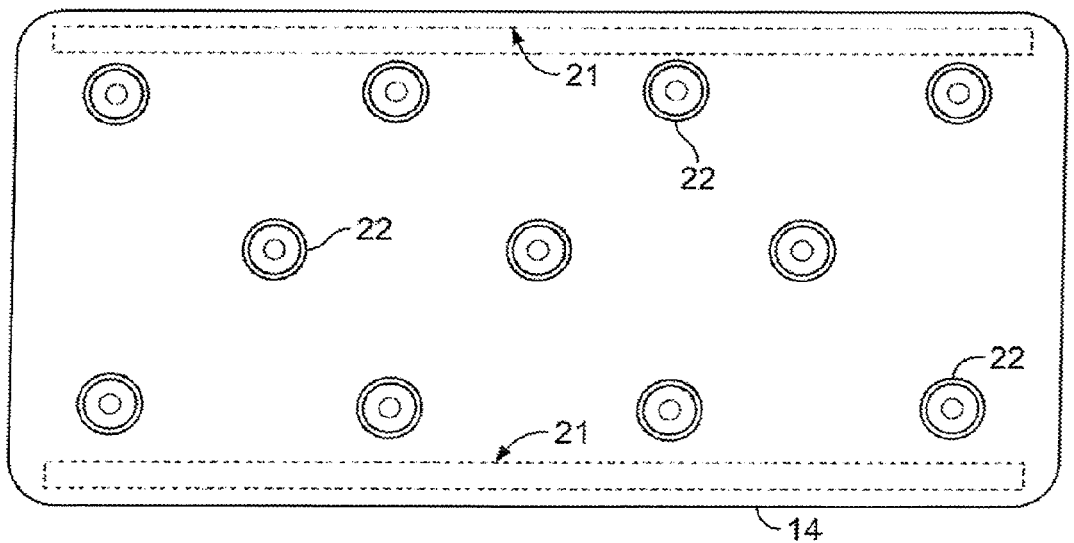
FIG. 5 is a bottom view of the mat of FIG. 1.
Figure 6:
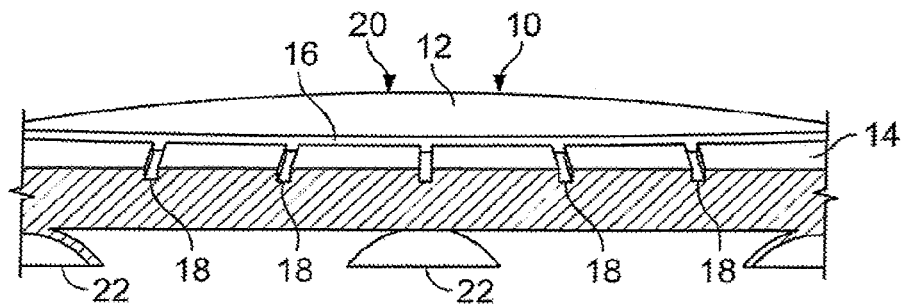
FIG. 6 is a fragmentary, cross-sectional view taken a long line 6-6 FIG. 1.
Figure 7:
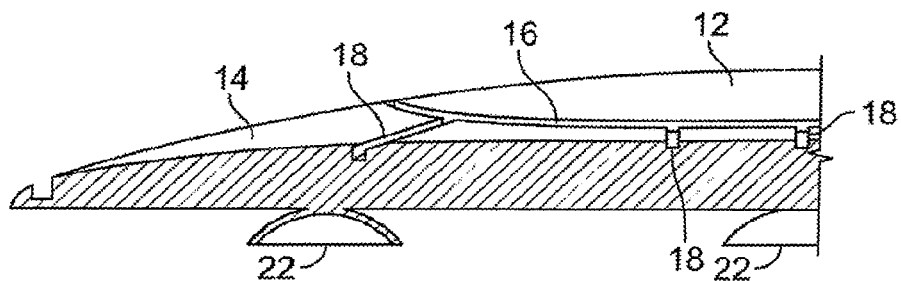
FIG. 7 is a fragmentary, cross-sectional view taken a long line 7-7 FIG. 1.

Referring to FIGS. 1-7, the illustrated floormat 10 may be made of an elastomeric material such as PVC, or a rubber, either synthetic or natural. Other materials such as polyurethane foam, a Amemory foam as well as materials commonly used in anti-fatigue mats are contemplated also. It is also desirable to make the mat material nonflammable, and to avoid allergic reactions, latex-free. In addition, the mat material contains static-dissipative properties ($10^9$ ohms per sq. ft.) and an anti microbial agent. Further, the mat material may be non-staining, UV resistant and resistant to most chemicals. The disclosed embodiment, designed specifically for antifatigue use and surface drainage, is made with chemically expanded closed-cell foam, manufactured with 100% virgin raw material having the specifications outlined in Table 1. It is appreciated that the specifications may vary for other embodiments.

TABLE 1

| GAUGE: | 650 mils | Tolerance |
|---|---|---|
| | (5/8 inch) | +/− 12 mils (+/− 0.012 inch) |
| WEIGHT/AREA: | 128 oz/yd$^2$ | Tolerance |
| | | (+/− 5 oz./yd$^2$ minimum) |
| DENSITY: | 17 lb/ft$^3$ | Tolerance 1 lb/ft$^3$ |
| HARDNESS: | 40-50 | Durometer Hardness |
| | | ASTM D-2240-86 |
| TENSILE STRENGTH: | 125 lb/in$^2$ minimum | Tensile Strength, Die > C = ASTM D-638-90 |
| ELONGATION @ 100%: | 130% | Elongation ASTM D-638-90 |
| TEAR STRENGTH: | 30 lb/in$^2$ minimum | Tear Strength ASTM D-1004-90 |
| FLAME RESISTANCE: | Pass | Federal Motor Vehicle Safety Standard 302 Flame Resistance |
| FLAME RESISTANCE: | Pass | Methenamide Pill Test DOC FF 1-70 |
| LIMITED OXYGEN INDEX: | >24% | ASTM D-2863-77 |
| OPERATING TEMPERATURE RANGE: | 30 F.- 110 F. | Manufactured by an ISO 9001:2000 certified company |

It is highly desirable to provide a mat 10 that is disposable and intended for a single use. Accordingly, the mat material need not be highly durable and wear-resistant. For such disposable models, wear resistant coatings are not contemplated. To keep mat 10 sanitary, it can be cleaned, disinfected or sterilized, as appropriate. Thereafter mat 10 can be rolled up or packaged flat in a plastic material before shipment.

Mat 10 as shown is 36 inches long (0.9 m) and 17 inches (0.4 m) wide, although other overall dimensions are contemplated for other embodiments. Mat 10 has a central section 12 encircled by an annular, tapered apron 14. Apron 14 is about 3.5 inches (8.9 cm) and has a slope that ranges between about 4 degrees to 30 degrees.

Central section 12 is crowned, that is, it slopes downwardly in every direction away from its apex 20, which is located at the center of the mat 10. In one embodiment the radius of curvature along the longitudinal centerline of the central section 12 is about 260 inches (6.6 m). In that embodiment the radius of curvature along a transverse centerline is about 58 inches (1.5 m). The advantages of crowning as described hereinafter will occur when the radius of curvature in central region 12 is less than a maximum of 500 inches (1.3 m). In one embodiment central section 12 has a thickness or height of 0.75 inch (1.9 cm) at its apex 20. It is desirable to have the height or thickness at apex 20 in the range of 0.5 to 1.5 inches (1.3 to 3.8 cm). With a thickness at apex 20 of about 0.75 inch (1.9 cm), the height or thickness of the central section 12 at its perimeter may be about 0.35 inch (9 mm), but for various other embodiments it will be desirable to keep the thickness at the perimeter in a range of 0.2 to 0.6 inch (5 to 15 mm).

The margin between central section 12 and apron 14 is marked by an optional, annular groove 16. The groove 16 runs parallel to the short sides and about 4 degrees to the long sides of mat 10 except at its rounded corners. Projecting outwardly and transversely from groove 16 across apron 14 are a number of channels 18. The width and depth of channels 18 are similar to that of groove 16, although they can be sized differently in other embodiments. Channels 18 will be sized to avoid tripping. In particular, channels 18 will be narrow enough to preclude any part of a user's shoe from lodging inside one of the channels. In one embodiment channels 18 were 0.25 inch (6 mm) wide and 0.06 inch (1.5 mm) deep, although this dimension can vary in alternative embodiments. It is advantageous to have these channels 18 in a range of ⅛ through 2 inch (3 through 13 mm) wide and 0.03 to 0.25 inch (0.7 to 6 mm) deep.

In most embodiments, central section 12 and apron 14 will be integral components that are molded at the same time to form a common core. A series of gutters 34, 36, 38, and 40 (sometimes referred to as intermediate gutters), in apron 14 around central section 12 communicate with the distal end of channels 18 and may be fitted with an optional drain assembly, having a structure that will be described presently. The height on both sides of gutters 34, 36, 38, and 40 are shown here as the same, and the side fed by channels 18 will be at least as high as the opposite side. Outlet gutter 42 (also referred to as an outlet) communicates with the junction of gutters 40 and 36 and allows drainage off floormat 24. In some embodiments the outlet gutter can be positioned differently and more than one outlet gutter may be employed.

A number of integral, molded suction cups 22 project from the underside of mat 10. In this embodiment suction cups 22 are molded simultaneously with the main body of the mat, that is, with central section 12 and apron 14. Suction cups 22 may be 0.5 to 1.5 inches (1.3 to 3.8 cm) in diameter, although other sizes are possible. In this embodiment three equidistant suction cups 22 are placed along the centerline on the underside of central section 12. On either side of this centerline two sets of four equidistant suction cups 22 are placed in lines parallel to the centerline to form a staggered, diamond pattern of suction cups. In other embodiments a different number of suction cups may be laid in a different pattern.

In some embodiments, suction cups will not be employed but the underside of the mat will have a nonslip surface. As shown in phantom in FIG. 5, a double sided adhesive tape 21 may be attached to the underside of the mat to keep it in place. The adhesive on the side of the tape attached to the mat would be a permanent adhesive, while the adhesive on the exposed surface would be repositionable. Tapes of this type are available from 3M. A paper liner could be employed to cover the adhesive during shipment and storage. Alternatively, the entire underside of the mat may be finished with a tacky substance or an adhesive. In other embodiments, the mat material itself may be inherently nonslip. In still other embodiments the underside may be roughened or may have a large number of nubs that grip the floor. Alternatively, the underside may have a plurality of domed depressions that create suction when pressed onto the floor. Moreover, the top side of the mat 10 (section 12 and apron 14) can have a nonslip finish as well, which can be accomplished by providing a roughened surface. Alternatively, the mat material may contain a chemical agent, giving all surfaces of the mat a nonslip finish.

Various embellishments and decorations are contemplated for mat 10. In keeping with customary colors for operating rooms, mat 10 can be colored blue either by incorporating a die or by applying a colored coating to the mat. In some embodiments, central section 12 and apron 14 may be colored differently. Also, advertising logos may be placed at various positions on mat 10. For example, a drug brand may be advertised in large letters on the central section 12.

The operations of the floormat 10 of FIGS. 1-7 will be briefly described. The above described mat 10 is laid on the floor next to a location where a user or other personnel are expected to stand. Stepping on mat 10 will cause the suction cups 22 to grip the floor and hold the mat 10 in place.

Mat 10 is made of resilient, material that will increase comfort, reduce fatigue and, in general, ease the burden of standing during a long procedure. In addition, while the apron 14 is thinner, it is still sufficiently thick to provide a comforting, anti-fatigue effect. Also, channels 18 (as well as groove 16) are relatively small and do not substantially degrade the cushioning, anti-fatigue effect on apron 14. Also, these channels 16 and 18 are sufficiently small to avoid any risk of tripping.

During the procedure fluids may fall onto mat 10. Fluids falling on central section 12 will tend to shed from the surface and drain through channels 16 and 18. Fluids eventually flow into gutters 36, 38, and 40 before exiting through outlet gutter 42. Fluids falling on apron 14 will shed fluids directly or through channels 18.

Figure 8:
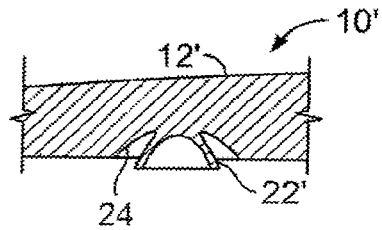
FIG. 8 is a detailed, fragmentary, cross-sectional view of a portion of a floormat with a recessed suction cup that is an alternate to that of FIG. 2.

Referring to FIG. 8, a modified mat 10' is arranged in a manner similar to that shown in FIG. 1. In this Figure, components corresponding to those previously illustrated in FIG. 1 will have the same reference numerals but marked with a prime ('). In particular, suction cup 22' has a shape similar to that previously illustrated but is located in a recess 23 on the underside of mat 10'. Suction cups 22' can be arranged in a pattern similar to that shown for the mat 10 of FIG. 1.

Referring to FIGS. 9-11, another floormat 24 is illustrated, again having rounded corners. Floormat 24 may be made of material similar to that described above in connection with the other embodiments and will have the previously mentioned adhesive tape (tape 21 of FIG. 5). In this embodiment the topside 26 is relatively flat except for a number of longitudinal channels 28. While twenty such channels are illustrated, other embodiments can have a greater or lesser number. Ridges 26A of topside 26 are located between channels 28. Gutters 134, 136, 138, and 140 encompass regions 26A and communicate with the distal ends of channels 28 (regions 26A being referred to as a central region having channels 28).

Outer border regions 26B, 26C and 26D are located to the outside of the gutters 134, 136, 138, and 140, which gutters are arranged similarly to the gutters of FIG. 1. Outlet 142 is aligned with gutter 140 at its intersection with gutter 136. Outlet 143 is aligned with gutter 140 at its intersection with gutter 134. In some embodiments one of the discrete outlet gutters 142 or 143 may be eliminated.

The floors of each of the channels 28 have a central peak 30 equidistant from the channel ends for dividing any fluids that enter the channels. The channels 28 are illustrated with a rectangular cross-section, although in other embodiments the cross-section may be semicircular, oval, polygonal, etc. Additionally, the width of the channels may vary along their lengths, in some embodiments.

The peaks of border regions 26B, 26C and 26D are all at substantially the same elevation as central region 26A. These outer regions 26B, 26C and 26D are beveled, sloping outwardly from their peaks to form the outer edge of the mat 24. Thus, these border regions 26B, 26C and 26D have a height no greater than that of gutters 134, 136, 138, and 140. Outer region 26B is approximately 2 inches (51 mm) wide, while outer region 26D is around 2 inch (13 mm) wide. Outer regions 26C are each 1 2 inches (38 mm) wide. All these dimensions may vary in other embodiments.

Channels 28 have a depth that increases for directions away from central peaks 30. Moreover, the elevation of the floors of channels 28 decline for directions away from central peaks 30. Accordingly, fluid entering channels 28 flows away from the central peak 30 to the channel ends and into the into the gutters 134 and 136, and, if present, the drainage pipes shown in FIG. 12.

In one embodiment floormat 24 has an overall length of 35 inches (0.9 m) and an overall width of 22 inches (0.56 m). In this embodiment the overall thickness of floormat 24 (measured at ridges 26A of topside 26) was 5/8 inch (16 mm). The channels 28 are 0.2 inch (5.1 mm) wide and are distributed with a channel to channel spacing (measured from the center of one channel to the center of another) of 0.7 inch (18 mm). The depth of the channels 28 varied linearly from a minimum of 1/8 inch (3.2 mm) at central peaks 30 to a maximum of 3/8 inch (9.5 mm) at the outlet ends. It will be appreciated that these dimensions and proportions can be varied for other embodiments.

The foregoing mat 24 may be made with nonslip surfaces in the manner described above for the other embodiments. Preferably, the underside 32 of the mat 24 will employ the double sided adhesive tape as shown in phantom in FIG. 5 and described for the other embodiments. Also, in some embodiments the entire underside 32 of the mat 24 may be finished with a tacky adhesive as described for the other embodiments, in order to keep the mat in place. Alternatively, the underside 32 of the foregoing mat 24 can have suction cups similar to those described above.

Figure 12:
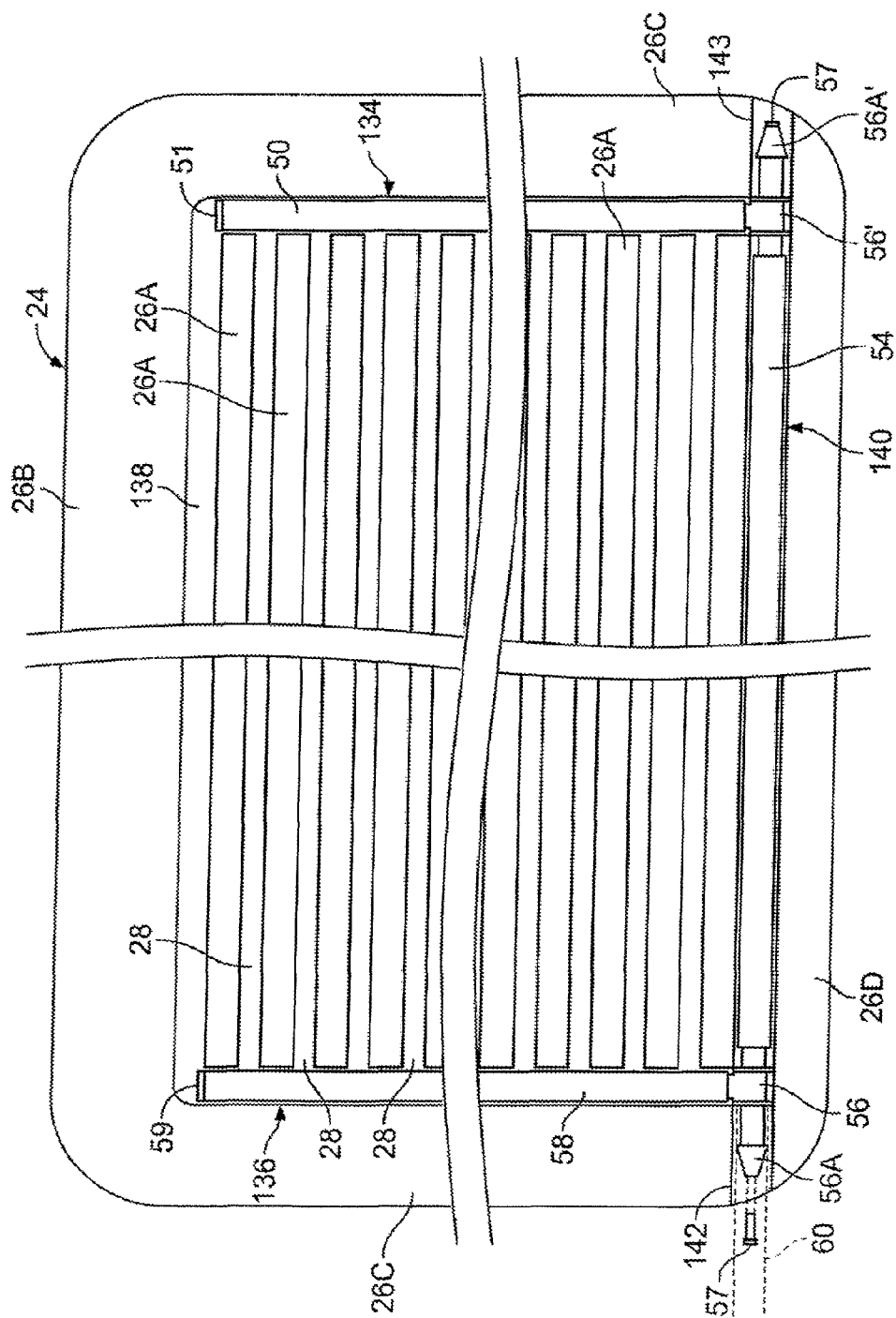
FIG. 12 is a detailed plan view of the floormat of FIG. 9 with portions broken away and with various tubes installed.

Gutters 134, 136, 140, 142 and 143 are each 2 inch in width to allow room to house the optional drainage assembly illustrated in FIG. 12. In most embodiments, gutter 138 will remain empty and will not be used to house any tubing or drainage pipes. Thus gutter 138 may be narrower than the other gutters, having a width of 0.3 inch (7.6 mm).

Figure 13:
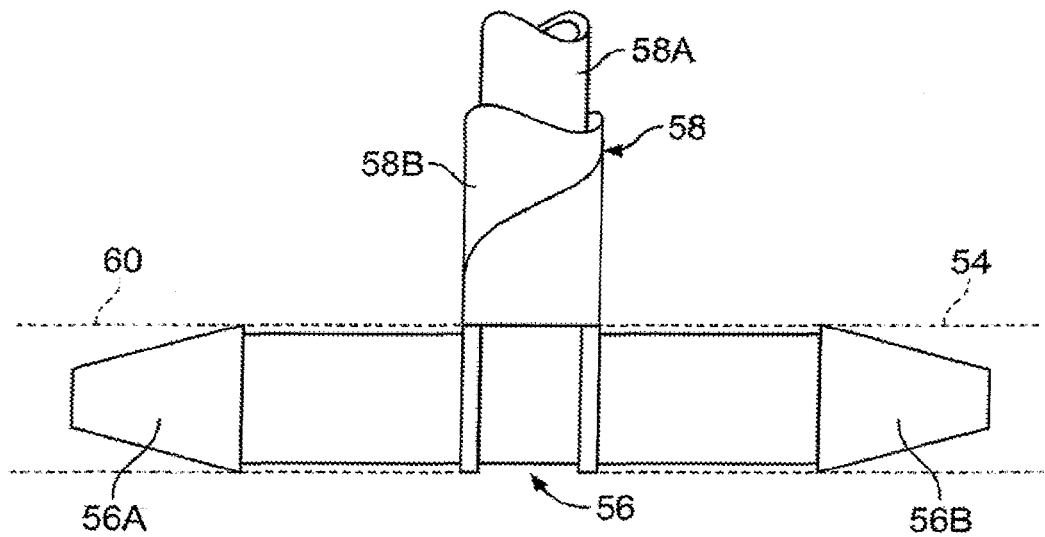
FIG. 13 is a plan view of a T-fitting in FIG. 12.
Figure 14:
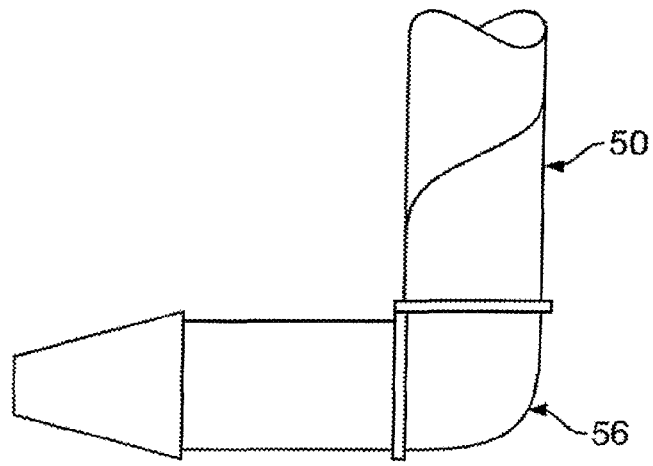
FIG. 14 is a plan view of an elbow that may be used in the floormat of FIG. 12.
Figure 15:
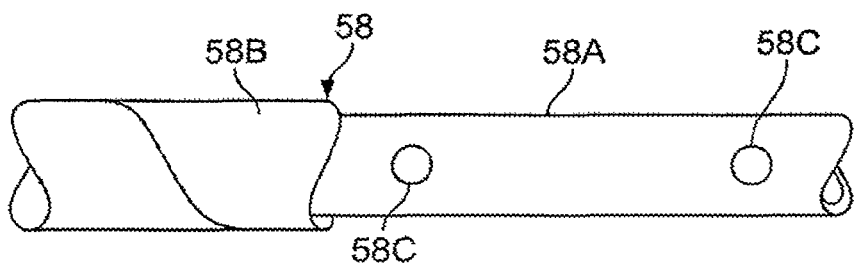
FIG. 15 is a side view of a fragment of a tube in FIG. 12.

Referring to FIGS. 12-15, FIG. 12 shows the mat of FIG. 9 fitted with a drain assembly, which is shown in further detail in FIGS. 13-15. In this modified arrangement, drainage pipes 50 and 58 (also referred to as tubing) will be placed in gutters 134 and 136, respectively. Pipes 50 and 58 may have identical structure and may be include tubing made of PVC or other materials.

Plug 59 is 0.47 inch in length (1.2 cm) and will be inserted in the distal end of pipe 50. The other end of pipe 58 will be fitted with one branch of T fitting 56, whose two other aligned branches lie in gutters 140 and 142. The branch of fitting 56 lying in gutter 142 (gutter 142 also referred to as an outlet) is shown as a conduit terminating in a conically flared head 56A designed to lock into tubing 60. When shipped, head 56A is sealed with removable plug 57, shown removed to accommodate tubing 60.

FIG. 13 shows the opposite branch, also in the form of a conduit terminating in a conically flared head 56B. The third branch of T fitting 56 is the same as the other two branches and its conical head is inserted into pipe 58. In this embodiment the outside diameter of the conical heads (e.g. head 56A) is 5/16 inch (8 mm), although other dimensions may be employed in other embodiments.

Plug 51 will be inserted in one end of pipe 50. The other end of pipe 50 will be fitted with one branch of T fitting 56', which is identical to fitting 56 on pipe 58. The two other aligned branches of fitting 56' lie in gutters 140 and 143. The branch of fitting 56 lying in gutter 143 (gutter 143 also referred to as an outlet) is shown as a conduit terminating in a conically flared head 56A=designed to lock into tubing, but in this case sealed with plug 57. Thus, a user can conveniently choose to connect tubing 60 to either head 56A or 56A=.

In some cases, fitting 56' (or fitting 56) may be replaced with elbow 52, shown in FIG. 14. In this case the proximal end of pipe 50 in gutter 134 will communicate through elbow 52 to pipe 54 in gutter 140, without communicating to gutter 143. Pipe 54 may be a simple plastic tube without the apertures or sleeves associated with pipes 50 and 58.

Referring to FIG. 15, drainage pipe 58 comprises plastic tubing 58A covered with a porous sleeve 58B. Tubing 58A may be made of a flexible plastic such as polypropylene, polyurethane or polyvinyl chloride with an outside diameter of 0.4 inch (1 cm), although other materials and dimensions may be employed in other embodiments. Sleeve 58B may be a polyester knit formed from a strip that is spirally wound and stitched to form a tube. Alternatively, a fabric strip can be curled back and stitched to form a straight, longitudinal seam. In other embodiments sleeve 58B may be knit or woven directly into a tubular form or may be formed of non-woven, porous materials that are fabricated in a tubular form. In all embodiments, sleeve 58B will serve as a noise reducer and debris filter. Sleeve 58B will have a size and flexibility chosen to reduce and dampen noise that might otherwise generated by vibrations in pipe 58. In some embodiments, sleeve may be a chamois-like material such as a non-woven viscose fabric.

Figure 16:
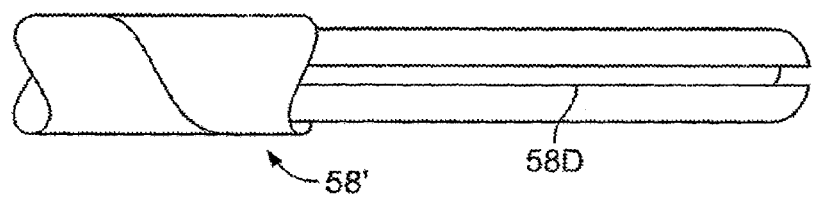
FIG. 16 is a side view of a tube that is an alternate to that of FIG. 15.

Tubing 58A has a series of longitudinally aligned, intake apertures 58C positioned to coincide with the outer end of channels 28, that is, one aperture for each of the channels 28. The diameter of apertures 58C may vary, though the preferred diameter is 1/16 inch (1.59 mm). In other embodiments these apertures may be replaced with the longitudinal slit 58D shown in FIG. 16, which is a feature of a pipe 58' that is otherwise identical to that shown in FIG. 15. Sleeve 58B prevents debris from passing through either apertures 58C (FIG. 15) or slit 58D (FIG. 16). Also, sleeve 58B acts as a dampener to provide some noise suppression.

Figure 17:
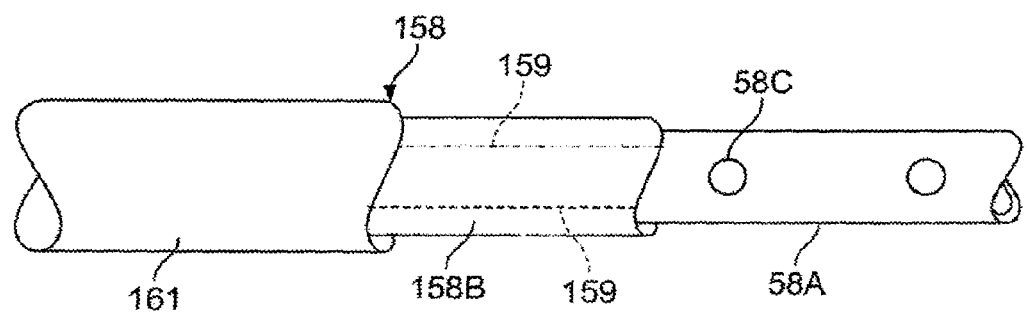
FIG. 17 is a side view of a tube that is an alternate to that of FIGS. 15 and 16.

Referring to FIG. 17, an alternate drainage pipe 158 has the same tubing as shown in FIG. 15 (tubing 58A). However, the spiral wrapped sleeve 58B is replaced with a strip 158B made of the same material. Strip 158B is laid longitudinally over apertures 58C and partially wrapped around the tubing 58A (for example 270°), leaving a gap between edges 159. In this embodiment strip 158B is a synthetic chamois-like material (e.g., nonwoven viscose fabric) designed to filter particles that might enter into aperture 58C, as well as providing mechanical dampening and noise suppression. Strip 158B is covered and held in place by braided sleeve 161, which also offers some coarse filtering. In one embodiment sleeve 161 was braided from PET yarns (e.g., a Flexo PET sleeve from Flextech Inc. of Sparta, N.J.).

Figure 18:
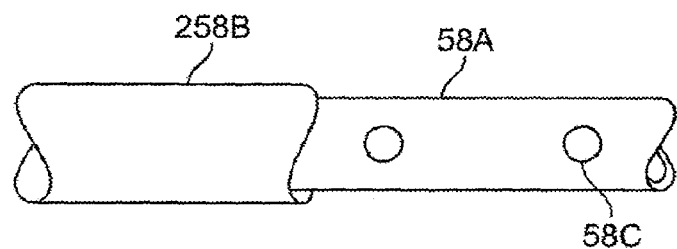
FIG. 18 is a side view of a tube that is an alternate to that of FIGS. 15-17.

Referring to FIG. 18, previously mentioned tubing 58A is covered with a sleeve 258B made of synthetic chamois-like material (e.g., nonwoven viscose fabric) either formed originally as a tube, or formed into a tube by joining two edges of an elongated strip. Again, sleeve 258B provides filtering and noise suppression.

Referring again to FIG. 12, flexible tubing 54 is shown lying in gutter 140 and connecting between the right branch of fitting 56 and the left branch of fitting 52. The left branch of fitting 56 will lie in gutter 142 and connect to a suction tube 60

(shown in phantom). Tubing 54 will lack the apertures and sleeve of pipes 50 and 58 and may be held in place by an adhesive such as cyanoacrylate or the like.

Pipes 50 and 58 may also be glued in place but only with a narrow bead of glue so that the sleeves (e.g., sleeve 58B) remain permeable and the apertures (e.g. apertures 58C) remain open. In this embodiment apertures 58C (or 58D) will point at a depressed angle of elevation of about 45° below horizontal (between a 4 and 5 o=clock position). It will be appreciated that pipe 50 will be made and installed in a similar manner.

It will be further appreciated that although an outlet is shown in one corner of the mat as gutter 142, the outlet can be placed anywhere along the gutters of the mat. Further, multiple outlets may be created to allow the flexibility of alternate outlets or to permit connection of additional suction tubes 60. Some embodiments may have multiple outlets that have removable plugs or dams so the user can choose where to connect one or more suction tubes 60. On the other hand, some embodiments will have only one outlet gutter.

The foregoing drainage pipes (tubing) may be fitted in the gutters of the embodiment of FIGS. 1-7. The gutter system of FIGS. 1-7 has a similar configuration as described above with one significant exception: fitted in gutter 38 is a drainage pipe with apertures and sleeving as shown in FIG. 15 or 16. Accordingly, the width of gutter 38 will be equal to the width of the other gutters. Consequently, previously mentioned caps 51 and 59 are replaced with elbows (not shown) that connect to this drainage pipe within gutter 38. In addition, previously mentioned tubing 54 is replaced by a fourth drainage pipe, similar to that of FIG. 15 or 16. For the pipes of FIG. 15, the apertures 58C are spaced to align with the outer end of channels 18. Also, because gutter 42 is the only discrete outlet gutter the elbow of FIG. 14 will be installed at the junction between gutters 34 and 14.

To facilitate an understanding of the principles associated with the foregoing apparatus, the operation of the embodiment of FIG. 12 will be briefly described. The above described mat 24 may be removed from its plastic packaging (not shown). The paper liners (not shown) are removed from the underside of the mat, exposing the repositionable adhesive tape (tape similar to tape 21 of FIG. 5). The mat 24 can then be positioned and laid on the floor at the location where a user or other personnel are expected to stand. Stepping on mat 24 will cause the adhesive tape 21 to grip the floor and hold the mat 24 in place.

Mat 24 is made of resilient material that will increase comfort, reduce fatigue and, in general, ease the burden of standing during a long procedure. Also, channels 28 are relatively small and do not substantially degrade the cushioning, anti-fatigue effect. Also, these channels 28 are sufficiently small to avoid any risk of tripping. Furthermore, the tops of ridges 26A are all at the same elevation so that the topside of mat 24 feels essentially flat to a person standing on the mat. In particular, while the floors of channels 28 are pitched to drain away from peak 30 (FIG. 9) a person standing on the mat 24 will not feel that pitch and will not feel off-balance.

During the procedure fluids may fall onto mat 24. Fluids tend to fall into channels 28 and flow away from peak 30 (FIG. 9) toward gutters 134 and 136. Suction applied by hose 60 through head 56A will create a vacuum in pipes 50, 54 and 58. Accordingly, fluid flowing to the ends of channels 28 will be sucked into the apertures 58C of pipes 50 and 58. Since the apertures 58C point slightly downwardly they will efficiently aspirate the draining fluid. Debris or other particles in the fluid will be filtered by sleeve 58B (embodiment of FIG. 15) or by sleeves 158B and 161 (embodiment of FIG. 17), or by sleeve 258B (embodiment of FIG. 18). Also, the foregoing sleeves can suppress noise caused by vibration in tubing 58A.

The suction applied by hose 60 through head 56A will create a vacuum in pipes 50, 54 and 58. Accordingly, fluid flowing to the ends of channels 28 will be sucked into the apertures 58C of pipes 50 and 58. Debris or other particles in the fluid will be filtered by sleeve 58B (embodiment of FIG. 15) or by sleeves 158B and 161 (embodiment of FIG. 17), or by sleeve 258B (embodiment of FIG. 18). Also, the foregoing sleeves can suppress noise caused by vibration in tubing 58A.

Fluid in pipe 50 will flow through fitting 56', pipe 54 and fitting 56, before being evacuated through hose 60. Fluid in pipe 58 will flow through fitting 56 and be evacuated through hose 60, as well. Hose 60 may be connected to a suction system such as may be found in a hospital operating room.

Consequently, the user will have a dry place to stand with less chance of contaminated, corrosive or infected fluids seeping through any foot covering worn by the user. Also, a dry surface will reduce the chance of slipping and falling. In addition, a significant amount of cleaning is avoided if fluids are removed by suction instead of draining onto the floor. Thus there can be a faster turnover of the operating room. Moreover, there is less risk of cleaning personnel coming into contact with contaminated fluids and risking injury from infection, chemical exposure, etc.

If the user is expected to work in several locations, multiple mats can be placed at those sites. Of course, mats can be provided for other assistants in the vicinity.

If pipes are not used in the drainage system, the fluids will naturally drain through gutters 134, 136, 140 before exiting through outlet gutters 142 in 143 (unless one of the outlet gutters is blocked by a dam or other means).

Referring to FIGS. 19 and 20, the illustrated device employs previously mentioned floormat 24, which bears reference numerals identical to those previously mentioned. As previously mentioned, floormat 24 is formed of a compressible and resilient material with an antimicrobial agent. It will be appreciated that in some embodiments floormat 24 may be replaced with the floormat shown in FIG. 1.

Floormat 24 has a pair of opposing surfaces, the top one formed with a spaced plurality of channels 28 feeding intermediate gutters 134, 136, 138 and 140, which in turn feed discrete outlet gutters 142 and 143. As before, intermediate gutters 134, 136, 138 and 140 may be outfitted with pipes (tubing) 50, 54 and 58, and the associated fittings shown in FIG. 12. In that case, previously mentioned hose 60 provides a source of negative pressure.

Floormat 24 is shown stacked on rectangular absorbent sheet 62. In this embodiment floormat 24 is 21.5 inches (0.55 m) wide and 35 inches (0.89 m) long, although the size of floormat 24 can be tailored to accommodate the relevant work area; that is, the region where a user is expected to stand. In the illustrated embodiment, absorbent sheet 62 is 36 inches (0.9 m) wide and 56 inches (1.4 m) long, although different sizes may be used in other situations depending upon the size of the relevant work area; specifically, the region where fluids may be expected to fall. In one embodiment absorbent sheet 62 is a medical mat from ESP Evolution Sorbent Products LLC of Chicago, Ill.; item no. 225SCB-PLY-FlagShip.

Absorbent sheet 62 is shown extending peripherally from three sides of floormat 24, specifically, from the right and left sides along border regions 26C, and from the posterior side along border region 26B. In this embodiment the anterior side of floormat 24 along border region 26D is coterminous with an edge of absorbent sheet 62. This coterminous feature allows floormat 24 to lie close to the work area without absorbent sheet 62 bunching up on obstructions, such as the legs of an operating table, the wheel of an automobile, etc. In cases without nearby obstructions, absorbent sheet 62 may extend peripherally beyond the anterior side along border region 26D. In some cases the size of absorbent sheet 62 can be custom trimmed with a scissor or by using optional perforations in the sheet.

Sheet 62 is shown having two layers, one with a fluid absorbent face 62A and the other with a fluid impermeable face 62B. Surface 62A is adhesively attached to the underside of floormat 24 at nine circular spots 64. The underside of floormat 24 is referred to herein as a given one of the opposing surfaces. In one embodiment the adhesive spots 64 employ a medium viscosity cyanoacrylate adhesive, e.g., Apollo 2077 type adhesive from Cyberbond LLC of Batavia, Ill. It will be appreciated that in other embodiments different types of adhesives may be used and the adhesive may be laid in a different pattern or in a continuous layer essentially matching the entire underside of floormat 24. Some embodiments may use mechanical fasteners, such as staples, rivets, etc. In still other embodiments, absorbent sheet 62 will not be attached to floormat 24, which will allow freedom to adjust their relative positions.

Layer 62A may be a meltblown polypropylene material having an absorbency of $0.156$ ml/cm$^2$ ($0.03$ fluid ounces per square inch), although in other embodiments the absorbency can be in the range of $0.05$ to $0.5$ ml/cm$^2$. The actual absorbency will be chosen depending upon the environment and the expected amount of fluid to be absorbed. In other embodiments layer 62A may be made of other fibrous material such as spunbond plastics, felt, etc., or may be made of other woven or knitted fabrics using natural or synthetic fibers.

Layer 62B faces down and may be a flexible sheet made of polyethylene or other materials. In most embodiments layer 62B will be selected to provide fluid impermeability. Layer 62B may be bonded to layer 62A and in most embodiments will have a slip resistant surface.

The foregoing device 24/62 may be used in an operating room where a surgeon must often deal with fluids spilling in the vicinity where the surgeon is standing. Many surgical procedures involve the discharge of bodily fluids or the washing or irrigation of various sites, all tending to result in spills, either intended or unintended. Keeping the surgeon's feet dry will reduce the danger of slipping and falling. Also spills occurring in an operating room may represent a biohazard and care must be taken to avoid seepage through footwear making contact with the skin. While handling fluid in the vicinity is an important consideration, preventing user fatigue is also important. The resilient surface presented by the foregoing floormat 24 will reduce user fatigue, while it and absorbent sheet 62 will also deal with spilled fluids. Also, as described before, a person will not feel off-balance when standing on mat 24 because the tops of ridges 26A are flat and higher than the pitched floors of channels 28.

In addition, a significant amount of cleaning is avoided if fluids are captured by absorbent pad 62 instead of draining onto the floor. Moreover, the absorbent pad tends to reduce the risk of cleaning personnel coming into contact with contaminated fluids and risking injury from infection, chemical exposure, etc.

Various other environments exist where a person may be standing during a procedure and where fluid may be spilled in the vicinity of where the person stands. For example, boaters may stand on a deck that is periodically sprayed or splashed by seawater. In some cases the boater may need to operate, repair or clean equipment and seawater may drain from the equipment during the procedure.

Also fishermen and hunters may need to clean, dress and prepare their catch or kill. In such cases fluids may run onto the ground due to the release of body fluids or water used to clean the work site. Butchers will experience a similar situation when cutting and dressing meat at a butcher shop.

In addition, many technicians and hobbyists in the automotive field, gun repair/maintenance field, or other mechanical repair fields may spill fluids used to clean parts or may spill fluids used by the machinery (hydraulic fluid, coolant, brake fluid, transmission fluid, refrigerant, etc.)

Ordinary consumers may also deal with spills in the vicinity of where the person stands. Fluids are often encountered when preparing foods or using the sink in a kitchen. In addition, various cleaning or repair tasks conducted throughout the house or the yard may involve fluid spills as well.

In all these instances one wishes to avoid standing in spilled fluids. In some cases avoiding the discomfort of wet feet is an important consideration, but in other instances the fluids involved can be hazardous or deleterious. For example, some fluids can be slippery and increase the danger of falling. Other fluids may be corrosive and can damage either footwear or the foot itself.

In operation, the device 24/62 of FIGS. 19 and 20 is placed at a workstation with absorbent sheet 62 down and floormat 24 up. Layer 62B will have a slip resistant surface to avoid slippage of the device. A user will stand on floormat 24 facing anterior border region 26D, as indicated by the outline of feet F. Although a user will feel most comfortable standing on floormat 24, the user may occasionally step off the floormat and place one or more feet on absorbent sheet 62.

As noted, the workstation may be adjacent an automobile, a surgical table, or other work area. The device 24/62 is oriented so the anterior border region 26D is closest to the work area that the user is facing, as indicated by feet F. Thus, absorbent sheet 62 does not extend into the work area and impinge on obstructions such as the legs of a surgical table, an automobile wheel, or the like.

As illustrated, gutters 134, 140, 136, and 138 have no tubing, and each therefore over most of its length are free from obstruction that would prevent fluid from fully filling the gutter and forming a single stream that is exposed on top. In some cases suction may be applied to the gutters 134, 136, and 140 through a fittings (e.g., see fitting 56 and 56' of FIG. 12) may be placed in outlets 142 and 143 (or one of them, in which case the other one is blocked).

In other cases, floormat 24 may be optionally fitted with tubing (pipes) as shown in FIG. 12 (pipes 50, 54 and 58 in intermediate gutters 134, 140 and 136, respectively). In this case tubing 50, 52, and 58 will each occupy at least most of the length of it respective gutter 134, 140, and 136. Therefore, in the manner previously described, fluid falling on floormat 24 can drain through channels 28 into these pipes and eventually be sucked into a suction tube (tube 60 of FIG. 12). Again, this greatly reduces cleanup and reduces the risk of personnel coming into contact with the foregoing fluids.

In addition, fluid may fall directly on absorbent sheet 62 as indicated by fluid drop D in FIG. 20. Sheet 62 will have sufficient absorbency to accommodate fluid spills that might be expected at the workstation. In addition, for instances where no suction is used to remove fluids from floormat 24, fluids may be shed through outlets 142 and 143 to be absorbed onto absorbent sheet 62.

Once the procedure is completed, floormat 24 and absorbent sheet 62 can be folded or rolled in order to trap captured fluids within the device. Personnel can remove the mat 24 and sheet 62, place it into a leakproof disposal bag and discard them. Often, the device 24/62 will require special handling since it may contain material considered corrosive or biological waste representing a danger of infection or contamination.

Figure 21:
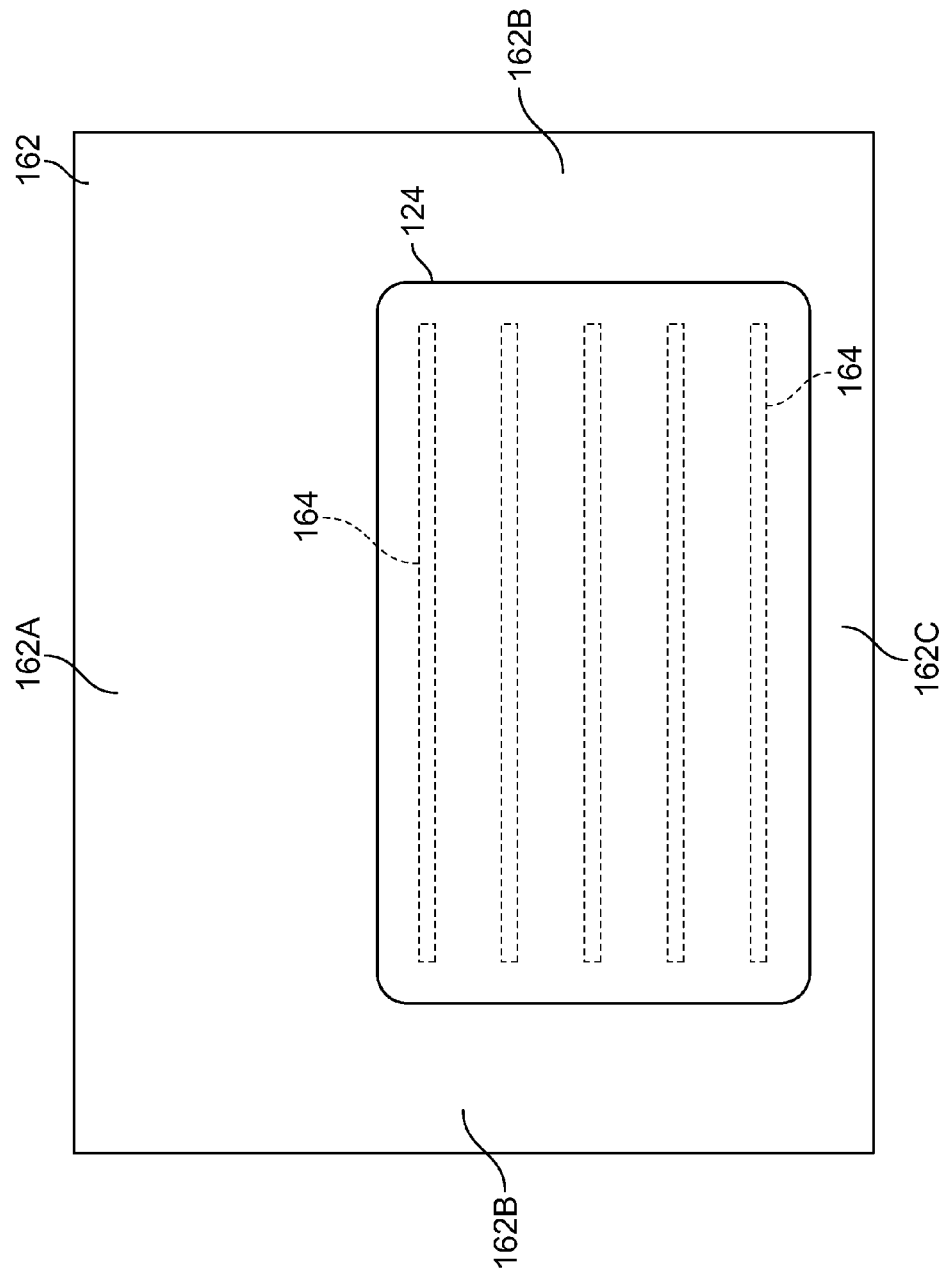
FIG. 21 is a plan view of a device that is an alternate to that of FIG. 19.

Referring to FIG. 21, the illustrated embodiment has an absorbent sheet 162 that may be structured in the same manner as the one previously described (sheet 62 of FIG. 19). Floormat 124 may be made of the same material as before and have the same overall width, length and thickness as the previously mentioned floormat (floormat 24 of FIG. 19). In this embodiment floormat 124 has a flat topside and flat underside.

Floormat 124 and absorbent sheet 162 are stacked and attached together adhesively along five longitudinal lanes 164, using an adhesive of the types described previously in connection with FIGS. 19 and 20.

In this embodiment, absorbent sheet 162 has a somewhat different configuration, with posterior portion 162A deeper and side portions 162B narrower than that previously shown in FIG. 19. Also, anterior portion 162C is not coterminous with floormat 124 but provides an apron for capturing falling fluids. In cases where obstructions are encountered, portion 162C may be folded, or severed and discarded.

In this embodiment the absorbent layer of sheet 162 faces up and its fluid impermeable layer faces down. In some cases the device of FIG. 21 may be designed for inverted placement, so that floormat 124 touches the floor and is covered by absorbent sheet 162. For such an inversion, the fluid impermeable layer of sheet 162 is attached directly to floormat 124, allowing the absorbent layer of sheet 162 to face up and capture falling fluids.

The device of FIG. 21 can be used in the manner previously described in connection with the device of FIGS. 19 and 20. For embodiments where the entire underside of absorbent sheet 162 is designed to contact the floor, falling fluids are either absorbed directly on the sheet, or indirectly after draining off floormat 124. For embodiments where absorbent sheet 162 will overlay floormat 124, falling fluids are absorbed directly on the sheet over its entire area.

In either case, this device will be deployed, used, and discarded in a manner similar to that previously described.

Figure 22:
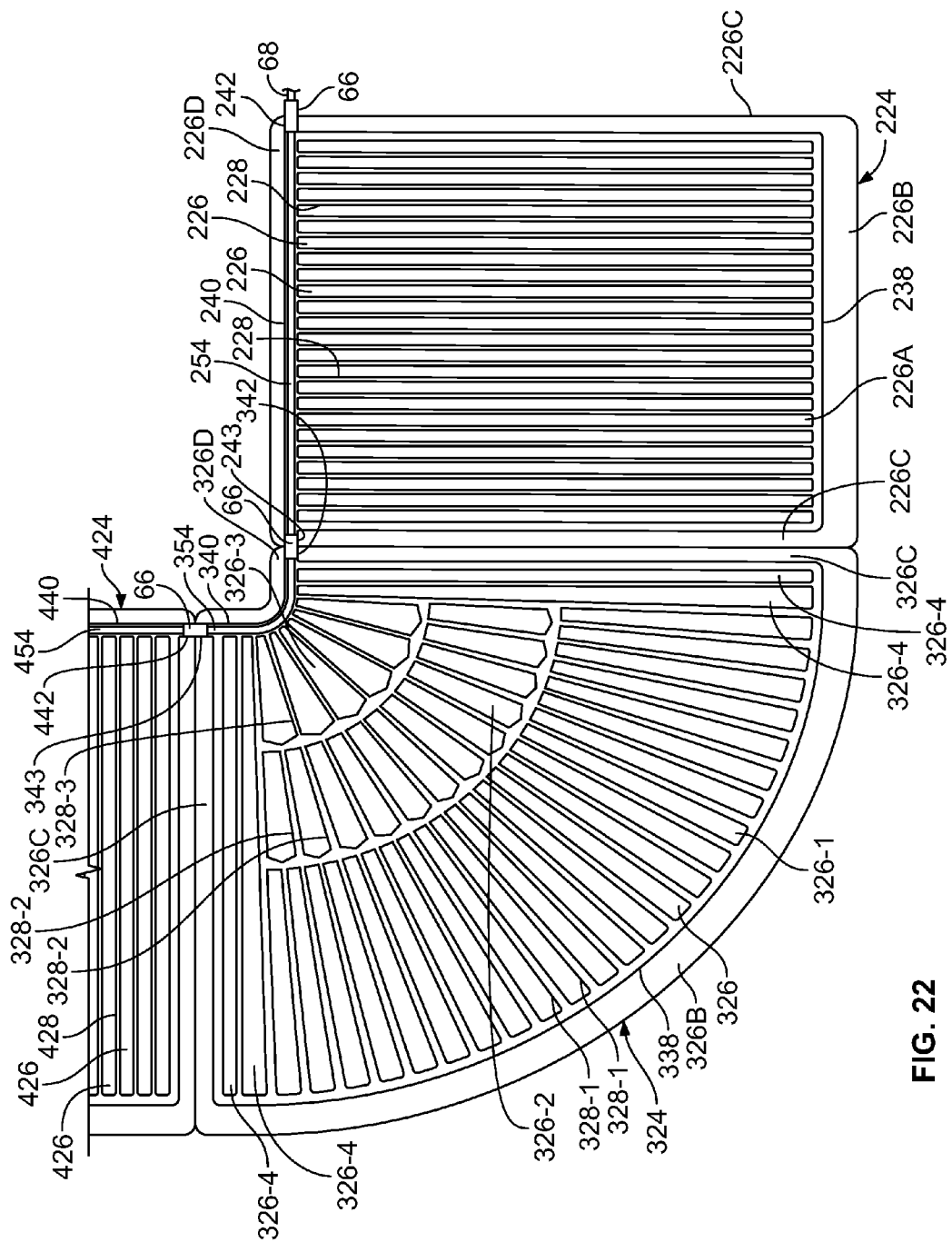
FIG. 22 is a plan view of a floormat having three mat sections that is an alternate to that of FIG. 9.
Figure 23:
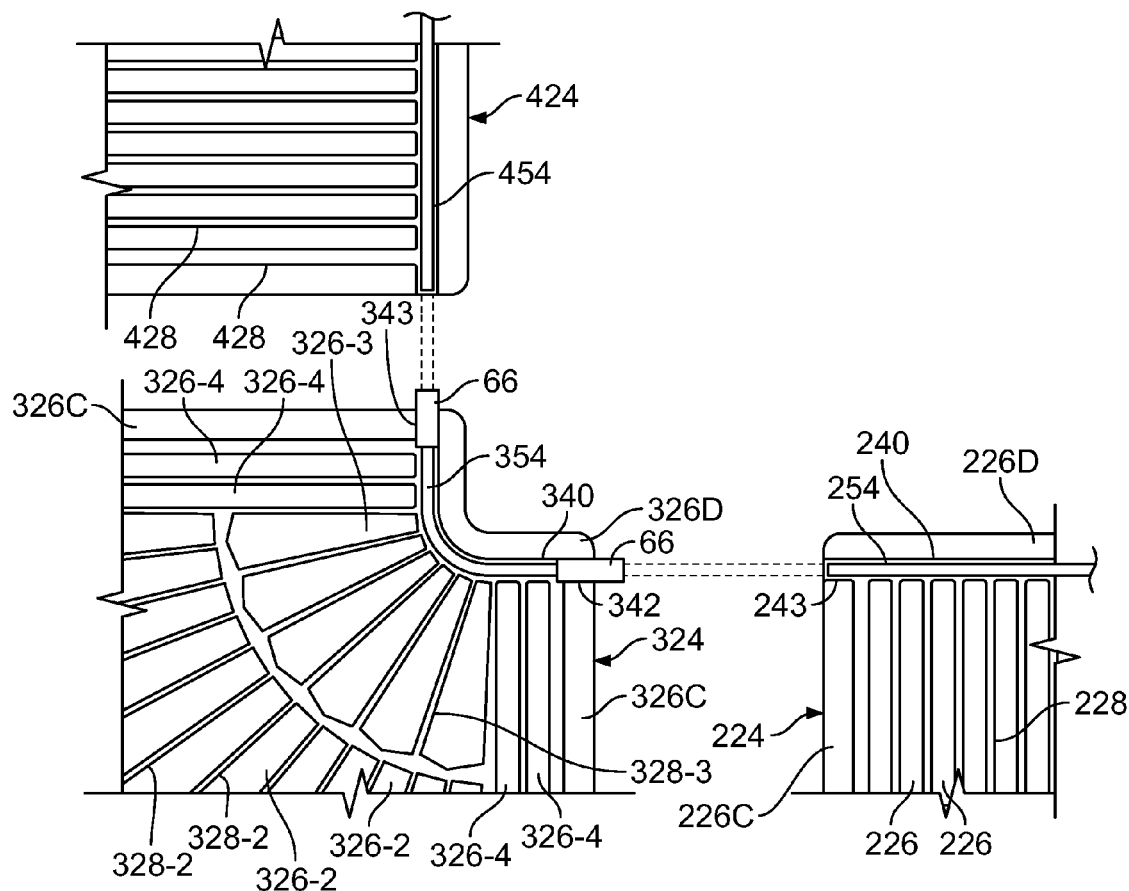
FIG. 23 is a detailed, exploded view of the mat sections of FIG. 22.

Referring to FIGS. 22 and 23, another floormat 224 is illustrated, with outer border regions 226B, 226C and 226D. Components in FIGS. 22-23 corresponding to those of FIG. 9-12 have the same reference numerals, but amended to have a A2" as the hundreds digit. Gutters 238 and 240 are arranged to the inside of borders 226B and 226D. Outlets 242 and 243 are aligned with intermediate gutter 240. In some embodiments one of the discrete outlet gutters 242 or 243 may be eliminated.

Floormat 224 may be made of material similar to that described above in connection with the other embodiments. In this embodiment the topside 226 is relatively flat except for a number of longitudinal channels 228 running between gutters 238 and 240. While twenty five such channels are illustrated, other embodiments can have a greater or lesser number. Ridges 226A of topside 226 are located between channels 228. Gutters 238 and 240 communicate with the ends of channels 228 (ridges 226A being referred to as being in a central region having channels 228).

The floors of each of the channels 228 may be pitched to drain toward gutter 240, although in some embodiments the channels may have a central peak (not shown) for dividing any fluids that enter the channels to either one of the gutters 238 and 240. In still other embodiments the channels may be level if one wishes to tolerate a certain amount of accumulation of fluids in the channels. The channels 228 may have a rectangular cross-section, although in other embodiments the cross-section may be semicircular, oval, polygonal, etc. Additionally, the width of the channels may vary along their lengths, in some embodiments.

The peaks of border regions 226B, 226C and 226D are all at substantially the same elevation as central ridges 226A. These outer regions 226B, 226C and 226D are beveled, sloping outwardly from their peaks to form the outer edge of the mat 224. Outer region 226B is approximately 2 inches (51 mm) wide, while outer regions 26D and 26C is around 1 inch (26 mm) wide. All these dimensions may vary in other embodiments.

Mat 224 is fitted with a drain assembly, specifically, drainage tube 254 is placed in gutter 240. Tube 254 may be tubing similar to that described in FIG. 15 with apertures aligned with channels 228. In some cases, one of the tubing embodiments of FIGS. 16-18 may be employed instead.

A corner mat 324 is illustrated, with outer border regions 326B, 326C and 326D. Components of mat 324 corresponding to those of mat 224 have the same reference numerals, but increased by 100. Border region 326B curves 90° between radially aligned borders 326C. Border region 326D provides an L-shaped inside corner and extends between border regions 326C. Gutters 338 and 340 are arranged to the inside of borders 326B and 326D. Outlets 342 and 343 (aka, outlet gutters) are aligned with intermediate gutter 340.

Floormat 324 may be made of material similar to that described above in connection with the other embodiments. In this embodiment the topside 326 is relatively flat and is composed of three curved bands of radially aligned ridges 326-1, 326-2, and 326-3, that are interleaved with longitudinal channels 328-1, 328-2 and 328-3, respectively. In addition, ridges 326-1, 326-2, and 326-3 are bordered on opposite sides by two spaced pairs of radially aligned ridges 326-4. Gutters 338, and 340 communicate with the channels 328-1, 328-2 and 328-3.

The floors of each of the channels 328-1, 328-2 and 328-3 may be pitched to drain toward gutter 340, although in some embodiments the channels 328-2 may be level or have a central peak (not shown) for dividing any fluids that enter the channels to either one of the gutters 338 and 340. The channels 328-1, 328-2 and 328-3 may have a rectangular cross-section, although in other embodiments the cross-section may be semicircular, oval, polygonal, etc. Additionally, the width of the channels may vary along their lengths, in some embodiments.

The peaks of border regions 326B, 326C and 26D are all at substantially the same elevation as central ridges 326-1, 326-2, and 326-3. These outer regions 326B, 326C and 326D are beveled, sloping outwardly from their peaks to form the outer edge of the mat 324. Outer regions 326B and 326D are sized to correspond with regions 226B and 226D, respectively.

Mat 324 is fitted with a drain assembly, specifically, drainage tube 354 is placed in gutter 340. Tube 354 may be tubing similar to that described in FIG. 15 with apertures aligned with channels 328-3. In some cases, one of the tubing embodiments of FIGS. 16-18 may be employed instead.

As shown in FIG. 22, floormats 224 and 324 are a separate pair of abutting mat sections with their outlet gutters 243 and 342 (aka, outlets) aligned. With this alignment tubes 254 and 354 are interconnected with union 66, which is in the form of a sleeve surrounding the adjacent ends of the tubes.

Also abutting mat section 324 is another mat section 424, which is essentially the same as floormat 224. Drainage tube 454 is placed in intermediate gutter 440. Tube 454 may be tubing similar to that described in FIG. 15 with apertures aligned with channels 328-3. In some cases, one of the tubing embodiments of FIGS. 16-18 may be employed instead.

Floormats 424 and 324 are a separate pair of abutting mat sections with their outlet gutters 442 and 343 (aka, outlets) aligned. With this alignment tubes 454 and 354 are interconnected with union 66.

This trio of mat sections 224, 324 and 424 forms a cooperating unit with common drainage through interconnected tubes 254, 354 and 454. A source of suction is provided from tube 68 (FIG. 22) which connects through union 66 to the downstream end of tube 254. Accordingly, suction source 68 can drain all three floor mats 224, 324 and 424 in a manner similar to that described for FIG. 9. It will be understood that the upstream end of tube 454 will be plugged (see as an example plug 57 of FIG. 12).

Unlike the embodiment of FIGS. 9-12, channel drainage will be from the outside to the inside, that is in a direction: (a) from gutter 238 to gutter 240, (b) from gutter 338 to gutter 340, and (c) from gutter 438 to gutter 440. Then drainage from channels 428 reaching drainage tube 454, will be carried to drainage tube 354. Also drainage from channels 328-1, 328-2 and 328-3 reaching drainage tube 354, will be carried to drainage tube 254. In addition, drainage from channels 228 reaching drainage tube 254, will be removed by suction tube 68. As before, removing fluids by suction reduces cleanup and reduces the risk of personnel coming into contact with dangerous substances.

It will also be appreciated that the ridges of mats 224, 324, and 424 (i.e., ridges 226, 326-1, 326-2, 326-3 and 426) will be at the same elevation, so a person standing on the mats will not feel off-balance, will feel a flat surface, and will not sense the pitched channels 228, 328-1, 328-2, 328-3, and 428.

Figure 24:
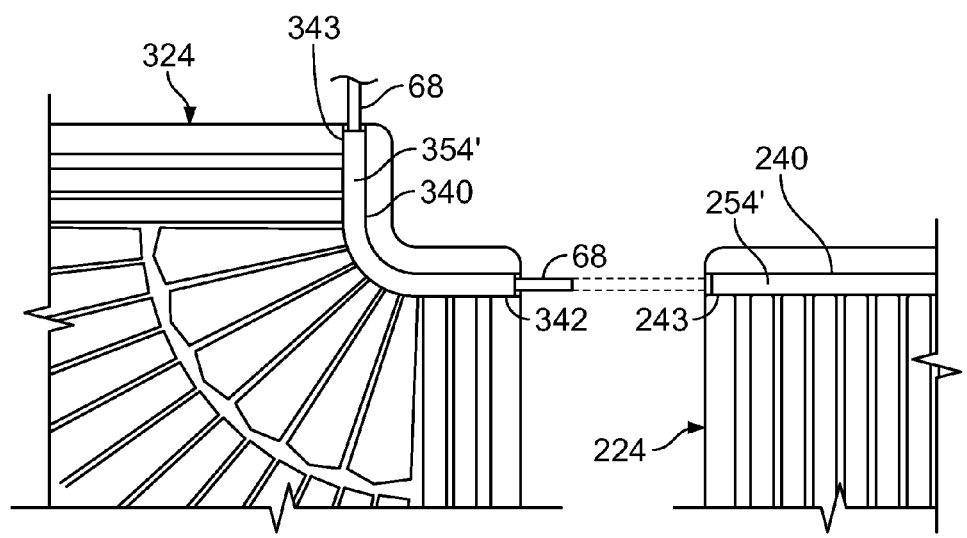
FIG. 24 is a detailed, exploded view of mat sections that are an alternate to that of FIG. 23.

Referring to FIG. 24, previously mentioned floormat 324 is fitted with a different tube 354', which has a somewhat larger diameter, filling more of the space within gutter 340. Likewise, gutter 240 of floormat 224 is fitted with a somewhat larger tube 254'. It will be appreciated that previously mentioned floormat 454 (not shown in FIG. 24) will also be fitted with a somewhat larger tube. Floormats 224 and 324 are shown separated but will normally be brought together in abutment, in which case reduced diameter tube 68 acts as a union, fitting inside the downstream end of tube 354' and the upstream end of tube 254' in order to connect them. Also, the upstream end of tube 354' will be connected by tube 68 to a larger drainage tube in previously mentioned floormat 424. In some embodiments tube 68 may have on either end a conically flared head similar to head 56A of FIG. 13.

Figure 25:
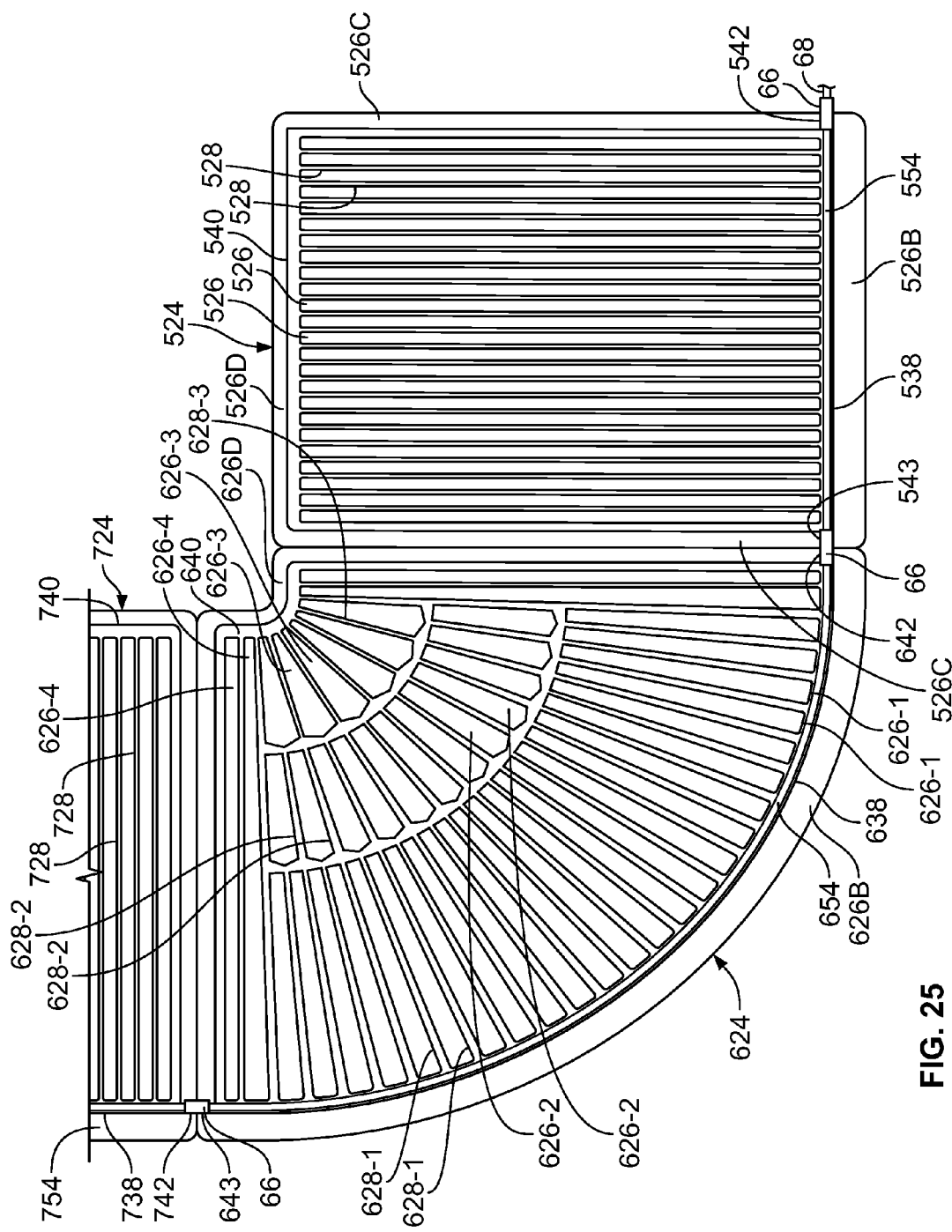
FIG. 25 is a plan view of mat sections that are an alternate to that of FIG. 22.

Referring to FIG. 25, mat sections 524, 624 and 724 are substantially the same as previously mentioned mat sections 224, 324 and 424, respectively, except for their gutters 538, 540, 638, 640, 738 and 740. Gutters 540, 640 and 740 are not fitted with tubes and for that reason can be made somewhat narrower. Intermediate gutters 538, 638 and 738 are fitted with tubes 554, 654 and 754, respectively. Tubes 554 and 754 may be identical to that previously described (i.e., identical to tubes 254 and 454 of FIG. 22). Tube 654 may be the same as previously mentioned tube 354 but much longer to accommodate the length of gutter 638. As before, tubes 554, 654 and 754 may be interconnected with previously described unions 66.

This trio of mat sections 524, 624 and 724 forms a cooperating unit with common drainage through interconnected tubes 554, 654 and 754. A source of suction is provided from previously mentioned suction tube 68 which connects through union 66 to the downstream end of tube 554. Accordingly, suction source 68 can drain all three floor mats 524, 624 and 724 in a manner similar to that described for FIG. 22. It will be understood that the upstream end of tube 754 will be plugged (see as an example plug 57 of FIG. 12).

Unlike the embodiment of FIG. 22, channel drainage will be from the inside to the outside, that is in a direction: (a) from gutter 540 to gutter 538, (b) from gutter 640 to gutter 638, and (c) from gutter 740 to gutter 738. Then drainage from channels 728 reaching drainage tube 754, will be carried to drainage tube 654. Also drainage from channels 628-1, 628-2 and 628-3 reaching drainage tube 654, will be carried to drainage tube 554. In addition, drainage from channels 528 reaching drainage tube 554, will be removed by suction tube 68.

Figure 26:
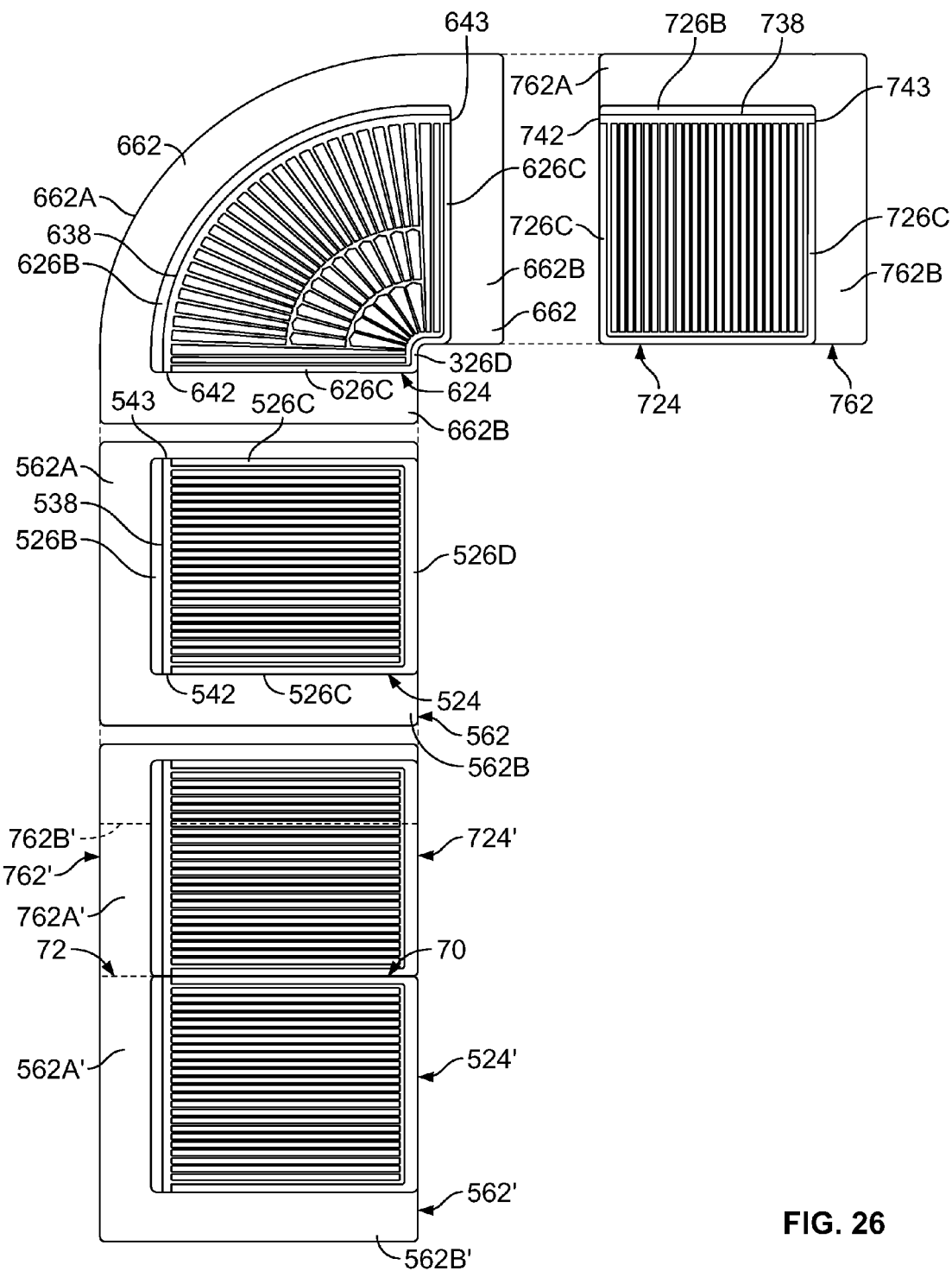
FIG. 26 is a plan view of mat sections, some sections previously shown in FIG. 25, and shown prior to assembly.

Referring to FIG. 26, previously mentioned mat sections 542, 642 and 724 are shown separated and stacked on absorbent sheets 562, 662 and 762, respectively. Sheets 562, 662 and 762 may be fabricated and attached to mat sections 542, 642 and 724 in the manner previously described in connection with FIG. 19. Sheet 562 is rectangular and extends outwardly from two adjacent sides of mat section 524, namely by means of extension 562A (next to region 526B) and right extension 562B (next to region 526C, i.e. the side furthest from mat section 624).

Mat section 724 has a similar, rectangular absorbent sheet 762 that extends outwardly from two adjacent sides of mat section 724, namely by means of extension 762A (next to region 726B) and left extension 762B (next to region 726C, i.e., the side furthest from mat section 624).

Mat section 624 has a similarly fabricated and attached absorbent sheet 662 shaped much like a quarter circle with a notched vertex and two rectangular extensions 662B spaced 90° apart and 662B extending away from region of 626C. Absorbent sheet 662 has extension 662A extending away from region 626B.

With this arrangement, mat 524 is readily abutted with mat 624 by placing mat 524 and its extension 562A over the adjacent extension 662B. Likewise, the other extension 662B is overlaid by mat 724 and its extension 762A.

In this embodiment, mat sections 524 and 724, as well as absorbent sheets 562 and 762 were previously joined together. Specifically, mat sections 524 and 724 were previously joined along the sides that face mat section 624 and are identified as regions 526C and 726C. Likewise, absorbent sheets 562 and 762 were joined together along the same sides and were originally part of a single continuous sheet.

Such a pre-separation condition can be observed in FIG. 26 by considering mat sections 524' and 724', which are integrally joined along seam 70. Except for this integral joint, mat sections 524' and 724' are identical to mat sections 524 and 724, respectively. Seam 70 may be a deep valley that allows severing of the mats 524' and 724' with a knife or scissor. Alternatively, mat sections 524' and 724' may be separate and disjoint, and only held together by being attached to a single common absorbent sheet 562'/762'.

Unitary absorbent sheet 562'/762' may be cut along the line 72 and along joint 70. In some embodiments sheet sections 562' and 762' may be perforated to facilitate separation along lines 72 and joint 70.

Absorbent section 762' is modified in order to abut mat section 724' with mat section 524 without interference. Basically, the normally extending extension 762B' is folded under as illustrated. Accordingly, extension 762B' does not cause interference when sheet extension 562B is overlaid with mat section 724' and extension 762A'. Instead of folding under, extension 762B' can instead be removed with a sharp implement or by bursting appropriately placed perforations.

Figure 27:
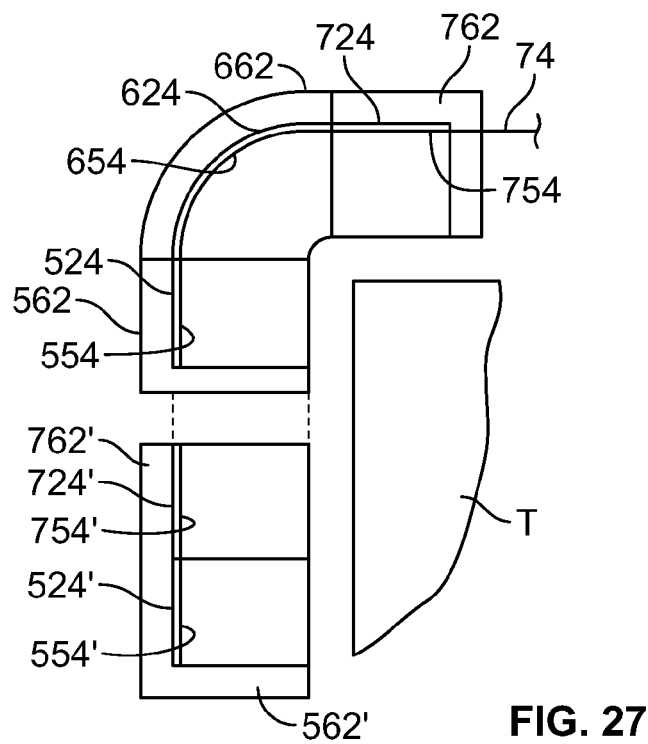
FIG. 27 is a plan, schematic view of the mat sections of FIG. 26, shown fitted with drainage tubes.

Referring to FIG. 27, previously mentioned mat section 624 is shown abutted with mat sections 524 and 724, which overlays absorbent section 662.

Previously mentioned drainage tubes 554, 654 and 754 are installed in mat sections 524, 624 and 724 in the manner previously described in connection with FIG. 25. The previously mentioned mat sections 524' and 724' are fitted with drainage tubes 554' and 754' in a manner similar to the installation of tubes 554 and 754. Upon abutment of mat sections 524 and 724' tubes 554 and 754' will be interconnected. All of the foregoing interconnections will be performed with the previously mentioned union (union 66 of FIG. 25).

Unlike FIG. 25, a suction tube 74 is connected to the distal end of drainage tube 754 instead of tube 554. The drainage received in tubes 554', 754', 554, 654, and 724 will flow through the tubes, in that order, and will be removed by suction tube 74.

The foregoing is shown arranged around surgical table T. Corner mat 624 effectively produces two branches that extend around the corner of the table T. It will be understood that these two branches can be lengthened or shortened as needed. If desired, additional mat sections can be used to border table T on three of four sides. Mat sections can be added to these branches as individual sections (e.g. mat sections 524 and 724) or as an integral pair of mat sections (e.g. mat sections 524' and 724'). In some cases, the mat sections will be added in a pattern that completely encircles table T.

Figure 28:
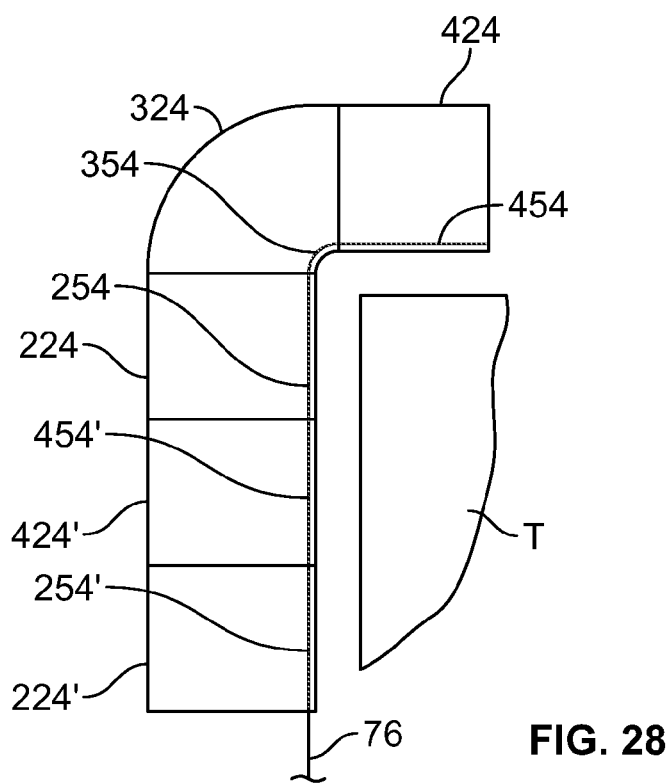
FIG. 28 is a plan, schematic view of mat sections fitted with drainage tubes that is alternate of that of FIG. 27.

A similar arrangement is shown in FIG. 28 using the mat sections of FIG. 22. As shown before, the trio of mat sections 224, 324 and 424 are fitted with interconnected drainage tubes 254, 354 and 454, respectively. Unlike FIG. 22, mat section 224 abuts with a pair of mat sections 224' and 424', which may be integrally joined in the manner previously shown (joint 70 of FIG. 26). Except for the integral joint, mat sections 224' and 424' are the same as mat sections 224 and 424, respectively.

Mat sections 224' and 424' are fitted with tubes 254' and 454', respectively, in a manner similar to that previously described for mat sections 224 and 424 in FIG. 22. In the embodiment of FIG. 28, however, tube 254 interconnects with tube 454'. In particular, drainage reaching interconnected tubes 454, 354, 254, 454', and 254' are evacuated, in that order, by suction tube 76 connected to the distal end of tube 254'. The interconnection between the foregoing tubes is accomplished with a union (e.g. union 66 of FIG. 22).

In this configuration, mats 524, 624, 724, 524' and 724' have the feel of a flat surface as described before in connection with FIG. 22. Therefore, a person standing on these mats will not feel off-balance.

Again, the use of absorbent sheets and the removal of fluid by suction streamlines cleanup and reduces the risk of injury to personnel that might otherwise come into contact with dangerous substances It is appreciated that various modifications may be implemented with respect to the above described embodiments. In some embodiments the floormat and absorbent sheet may have other than a rectangular outline; for example, an outline that is semicircular, hexagonal, other polygons, oval, curved, etc. While in some embodiments the absorbent sheet is shown extending from two or three sides of the floormat, in some cases those embodiments can be modified so the absorbent sheet extends from additional sides, e.g. from all sides of the floormat. In some cases the floormat may be perforated to allow direct drainage to an underlying absorbent sheet. In some embodiments the absorbent sheet will have an impermeable layer that is unbonded and free to move relative to the absorbent layer. In other embodiments, the absorbent sheet will have a pocket for holding the resilient format. In some instances, the floormat will be made of separate segments that are attached to a common absorbent sheet. While the illustrated grooves and channels are shown having a rectangular cross-section, in some embodiments their cross-section may be rounded, triangular, polygonal, oval, or shaped otherwise. Also in some embodiments the channels may be so close together that a cross-section through the mat reveals a sinuous or sawtooth pattern. Moreover, in some embodiments the path of the channels may be curved. In some cases, the paths of the channels may be in the form of nested arches or may be arranged in a herringbone pattern. In addition, the mats in some embodiments may have perforations that allow the fluids to pass directly through the mat. Furthermore, in embodiments like that of FIG. 1, not all of the channels will reach the border of the central section, and some channels may run across just the apron. Moreover, instead of a central section surrounded on all sides by an apron, in some embodiments the central section may be a center strip running across the full length of the mat and bordered on either side by a separate pair of tapered aprons.

Obviously, many modifications and variations of the present invention are possible in light of the above teachings. It is therefore to be understood that within the scope of the appended claims, the invention may be practiced otherwise than as specifically described.

The invention claimed is:

1. A device for handling fluids comprising:
a floormat having an opposing pair of surfaces including a plurality of edges, a topside and an underside, and being formed, at least in part, of compressible and resilient material, said topside having a spaced plurality of channels feeding at least one gutter on a side of the gutter that has a height at least as great as the opposite side thereof, said channels being sized to avoid a risk of tripping, said topside having a central region and a border region, said central region occupying most of said topside and being substantially flat throughout except for the channels, said border region having a height no greater than that of said at least one gutter, said at least one gutter having at least one outlet for draining fluid from said gutter, said border region lying along said plurality of edges and encircling said central region, said gutter lying alongside a first one of said plurality of edges, portions of said border region spaced from said first one of said plurality of edges having an outwardly tapered perimeter.

2. A device according to claim 1 wherein said at least one gutter is formed in said border region.

3. A device according to claim 1 wherein each of the channels have in the central region a sloping floor.

4. A device according to claim 1 wherein said border region on one or more sides of the floormat has an outwardly tapered perimeter, and is at least as wide as, said one or more gutters.

5. A device according to claim 4 wherein said at least one outlet comprises a spaced pair of outlets, drainage off said floormat being provided through one of said pair of outlets, the other one of said outlets being restricted from conducting fluid drainage.

6. A device according to claim 4 wherein said channels have a width of at most 0.5 inch.

7. A device according to claim 4 wherein said channels have a depth of at most 0.25 inch.

8. A device according to claim 1 adapted to cooperate with a source of suction, said floormat comprising:
a fitting mounted at said at least one outlet and adapted to attach to said source of suction.

9. A device according to claim 8 comprising:
porous material mounted at said fitting.

10. A device according to claim 9 wherein said porous material is a substance adapted to filter debris and reduce noise.

11. A device according to claim 10 wherein a predetermined portion of said border region lying along said first one of said plurality of edges is narrower than remaining portions of said border region that are spaced from said predetermined portion.

12. A device according to claim 11 wherein said border region on one or more sides of the floormat has an outwardly tapered perimeter, and is at least as wide as, said one or more gutters.

13. A device according to claim 1 wherein a predetermined portion of said border region lying along said first one of said plurality of edges is narrower than remaining portions of said border region that are spaced from said predetermined portion.

14. A device according to claim 1 comprising:
an absorbent sheet attached to a given one of the opposing surfaces of said floormat, at least part of the absorbent sheet being stacked to extend peripherally beyond the floormat.

15. A device according to claim 14 wherein the absorbent sheet is stacked to extend peripherally beyond the floormat on three sides of the floormat.

16. A device according to claim 14 wherein the absorbent sheet is stacked to extend peripherally beyond the floormat on three sides of the floormat, the floormat and absorbent sheet being coterminous on a fourth side of the floormat.

17. A device according to claim 14 wherein the absorbent sheet has a fluid impermeable face and a fluid absorbing face.

18. A device according to claim 17 wherein the fluid impermeable face of the absorbent sheet is slip resistant, the fluid absorbing face being attached to the given one of the opposing surfaces of the floormat.

19. A device according to claim 18 wherein the absorbent sheet is stacked to extend peripherally beyond the floormat on three sides of the floormat.

20. A device according to claim 1 wherein the at least one gutter over most of its length being free from obstruction that would prevent fluid from fully filling said gutter and forming a single stream that is exposed on top.

* * * * *